(12) United States Patent
Fabien et al.

(10) Patent No.: US 9,707,343 B2
(45) Date of Patent: Jul. 18, 2017

(54) AUTOINJECTOR COMPRISING A TIME DELAY DEVICE HAVING A PLANETARY GEAR SET FOR DELAYING THE RETRACTION OF THE NEEDLE

(71) Applicant: APTAR FRANCE SAS, Le Neubourg (FR)

(72) Inventors: David Fabien, La Buisse (FR); Antoine Mansencal, Langon (FR); Matthieu Walter, Le Vesinet (FR)

(73) Assignee: APTAR FRANCE SAS, Le Neubourg (FR)

( * ) Notice: Subject to any disclaimer, the term of this patent is extended or adjusted under 35 U.S.C. 154(b) by 153 days.

(21) Appl. No.: 14/398,994

(22) PCT Filed: May 24, 2013

(86) PCT No.: PCT/FR2013/051140
§ 371 (c)(1),
(2) Date: Nov. 5, 2014

(87) PCT Pub. No.: WO2013/175139
PCT Pub. Date: Nov. 28, 2013

(65) Prior Publication Data
US 2015/0119814 A1    Apr. 30, 2015

(30) Foreign Application Priority Data

May 25, 2012   (FR) ...................................... 12 54862
Sep. 27, 2012  (FR) ...................................... 12 59116
Mar. 21, 2013  (FR) ...................................... 13 52517

(51) Int. Cl.
*A61M 5/20*   (2006.01)
*A61M 5/32*   (2006.01)

(52) U.S. Cl.
CPC .......... *A61M 5/2033* (2013.01); *A61M 5/326* (2013.01)

(58) Field of Classification Search
CPC ................ A61M 5/2033; A61M 5/326; A61M 2005/2086
See application file for complete search history.

(56) References Cited

U.S. PATENT DOCUMENTS 6,464,663 B1 *  10/2002  Zinger ............. A61B 17/00491
                                                 222/390
2005/0273055 A1   12/2005  Harrison et al.
(Continued)

FOREIGN PATENT DOCUMENTS

EP     1 743 666 A1    1/2007
EP     2 399 628 A1   12/2011
(Continued)

OTHER PUBLICATIONS

International Search Report for PCT/FR2013/051140, dated Oct. 1, 2013.
(Continued)

*Primary Examiner* — Quynh-Nhu H Vu
(74) *Attorney, Agent, or Firm* — Sughrue Mion, PLLC

(57) ABSTRACT

An autoinjector comprising a lower body (10) receiving a tank, said tank containing fluid product and comprising a piston and a needle, such as a pre-primed syringe (A), said autoinjector comprising:
 injection means (5, 8) to inject said fluid product through said needle when said needle is in an injection position; and
 a tank movement device (2, 4, 9) for retracting said needle out of the body of the user after injection of the fluid product, a trigger (19), actuated by said injection means, actuating said tank movement device (2, 4, 9) after injection of the fluid product so as to retract said needle;

(Continued)

said autoinjector comprising a retarding device (15, 16, 17) adapted to delay during a predetermined time the actuation of said tank movement device (2, 4, 9) by said trigger (19) after injection of the fluid product, to delay retraction of said needle by said predetermined time after the end of injection.

11 Claims, 25 Drawing Sheets

(56) References Cited

U.S. PATENT DOCUMENTS

| | | | |
|---|---|---|---|
| 2006/0258990 A1* | 11/2006 | Weber | A61M 5/20 604/208 |
| 2008/0281271 A1 | 11/2008 | Griffiths et al. | |
| 2010/0049125 A1* | 2/2010 | James | A61M 5/2033 604/110 |
| 2010/0094214 A1 | 4/2010 | Abry et al. | |
| 2011/0028910 A1* | 2/2011 | Weber | A61M 5/2033 604/211 |
| 2013/0172822 A1 | 7/2013 | Ekman et al. | |
| 2013/0274655 A1* | 10/2013 | Jennings | A61M 5/20 604/67 |
| 2014/0207102 A1* | 7/2014 | Segal | A61M 5/3158 604/506 |

FOREIGN PATENT DOCUMENTS

| | | |
|---|---|---|
| EP | 2 399 632 A1 | 12/2011 |
| FR | 2 884 722 A1 | 10/2006 |
| FR | 2 905 273 A1 | 3/2008 |
| GB | 2463034 A | 3/2010 |
| WO | 96/32974 A1 | 10/1996 |
| WO | 2008/112472 A2 | 9/2008 |
| WO | 2009/037141 A1 | 3/2009 |
| WO | 2009/040602 A1 | 4/2009 |
| WO | 2009/040604 A1 | 4/2009 |
| WO | 2009/040607 A1 | 4/2009 |
| WO | 2009/062508 A1 | 5/2009 |
| WO | 2009/095701 A1 | 8/2009 |
| WO | 2010/108116 A1 | 9/2010 |
| WO | 2011/048422 A2 | 4/2011 |
| WO | 2011/101380 A1 | 8/2011 |
| WO | 2011/101382 A1 | 8/2011 |
| WO | 2012/000832 A1 | 1/2012 |
| WO | 2012/022810 A2 | 2/2012 |
| WO | 2012/045833 A1 | 4/2012 |

OTHER PUBLICATIONS

International Preliminary Report on Patentability from the International Searching in counterpart application No. PCT/FR2013/051140, date unknown.

* cited by examiner

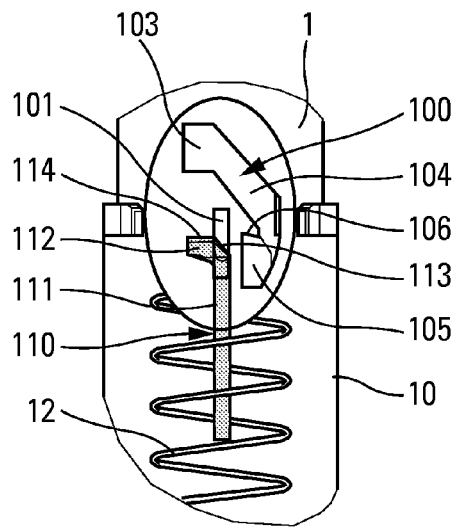
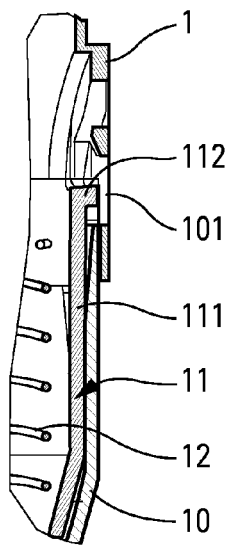
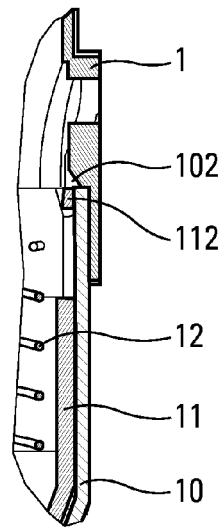
Fig. 4  Fig. 5  Fig. 6
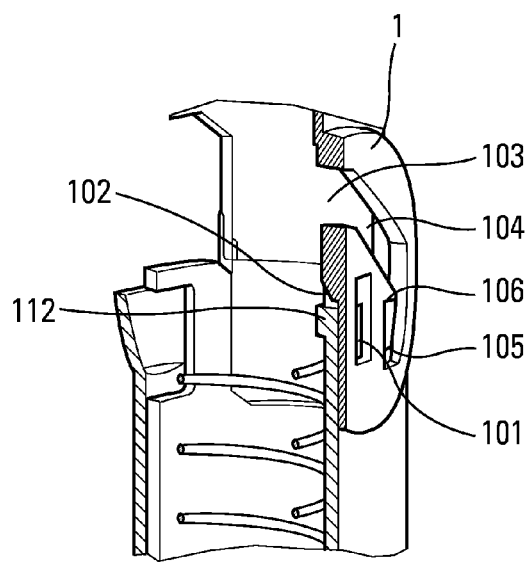
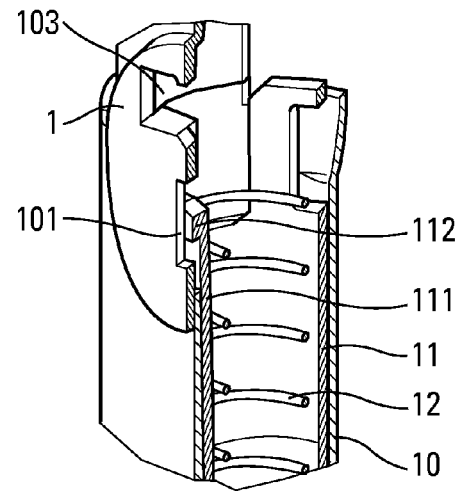
Fig. 7  Fig. 8

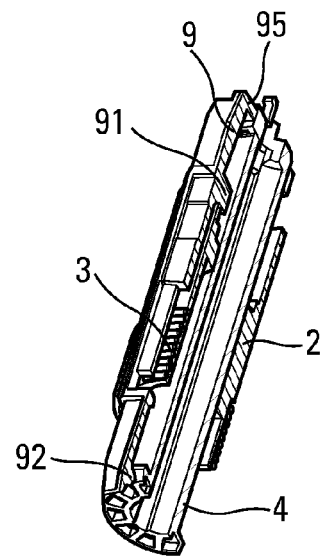
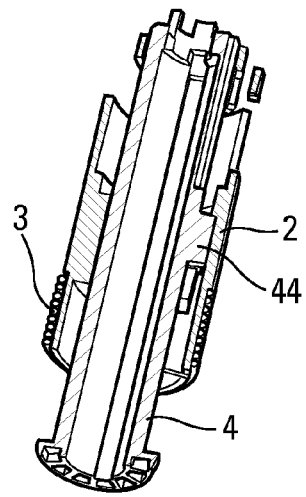
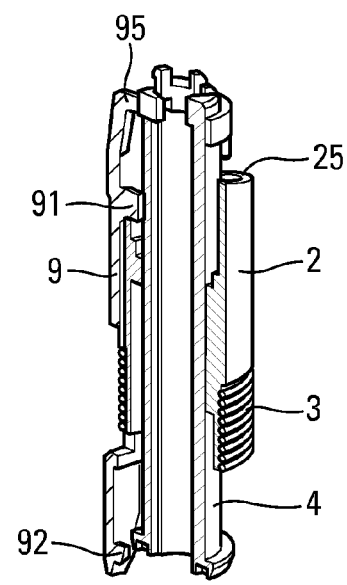
Fig. 33  Fig. 34  Fig. 35
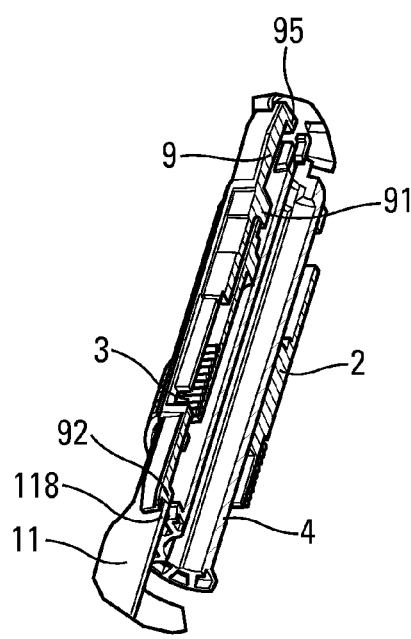
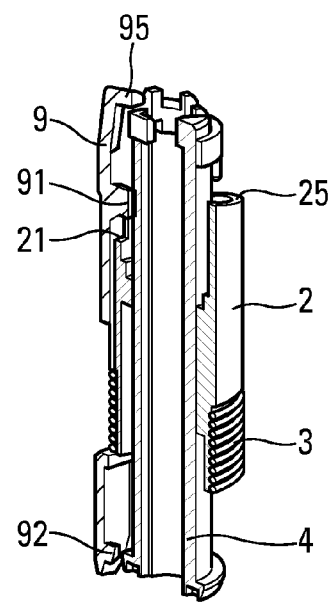
Fig. 36  Fig. 37

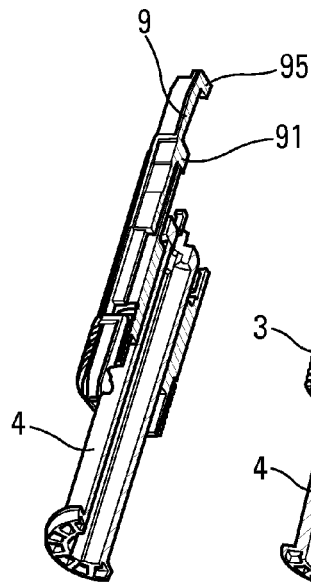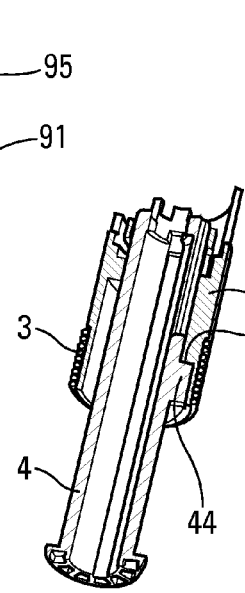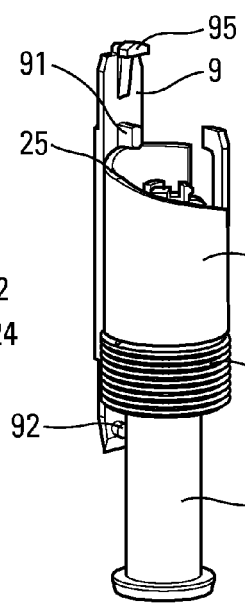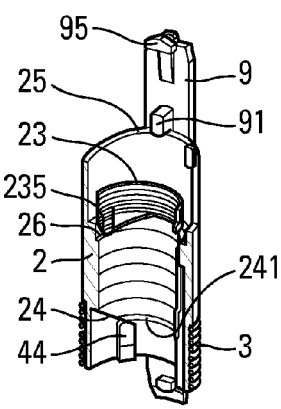
Fig. 38   Fig. 39   Fig. 40   Fig. 41
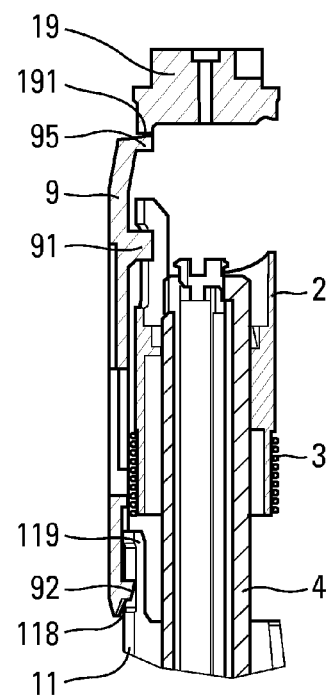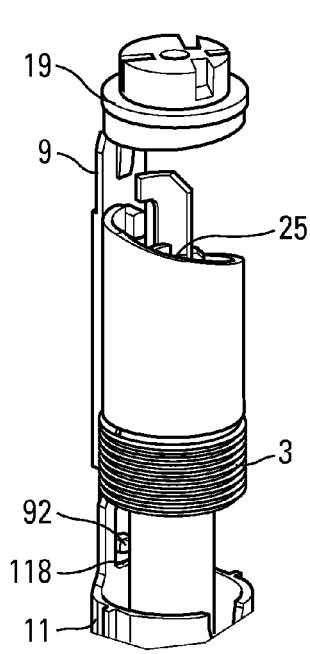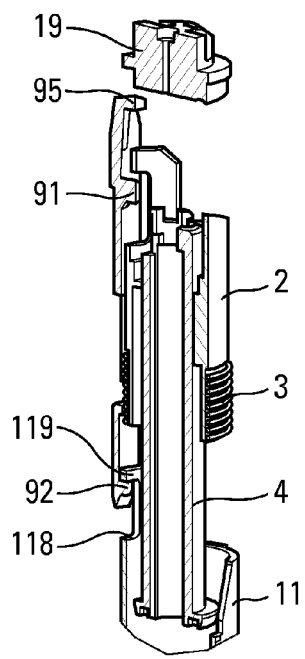
Fig. 42   Fig. 43   Fig. 44

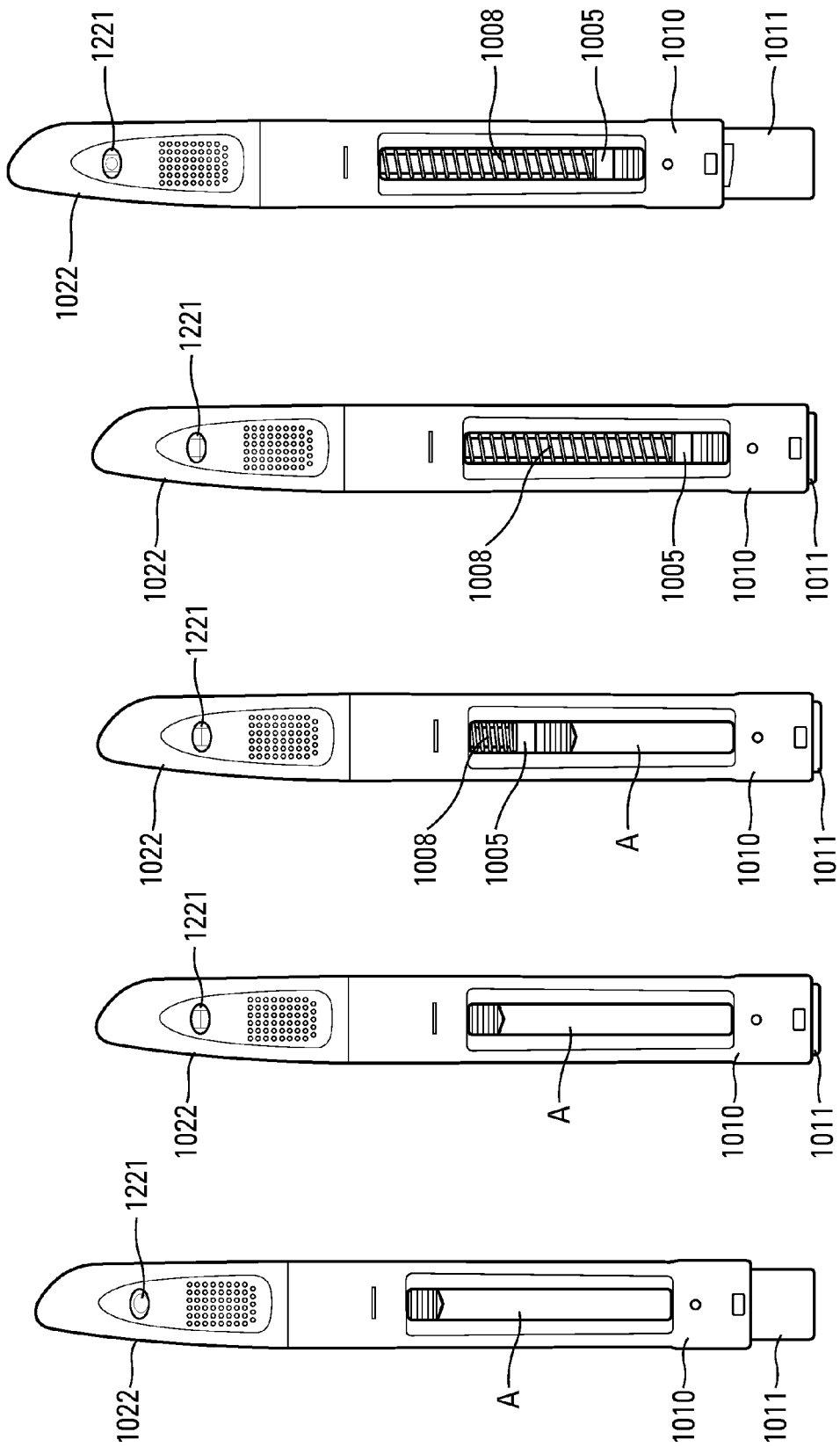

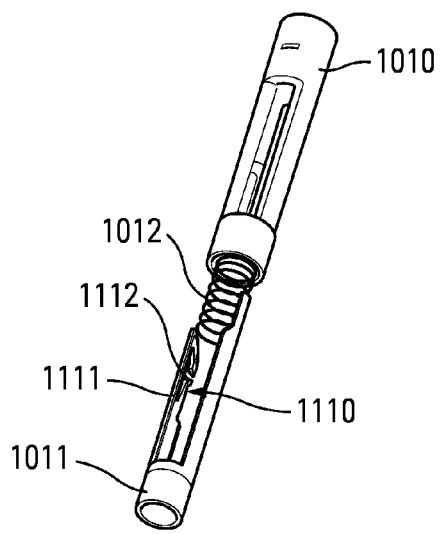
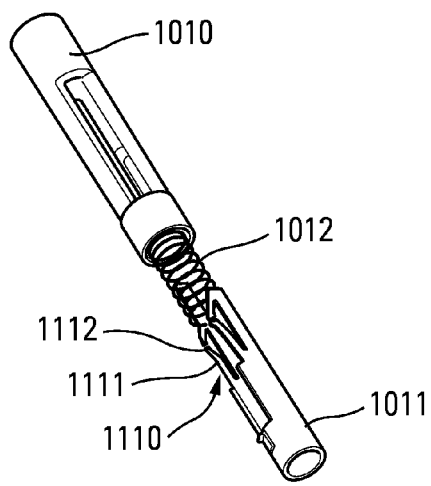
Fig. 49a　　　　　　　Fig. 49b
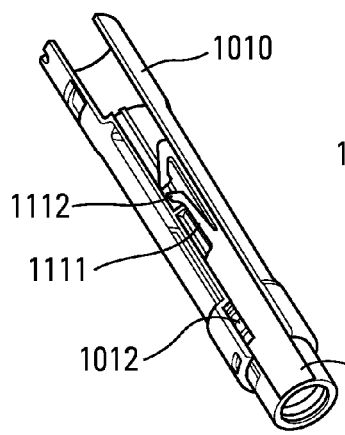
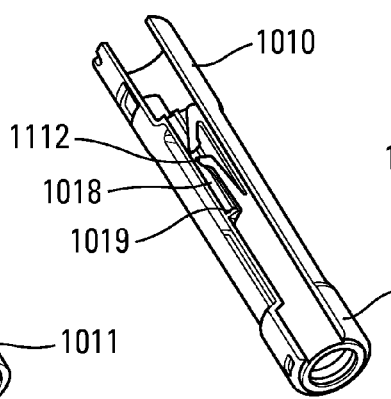
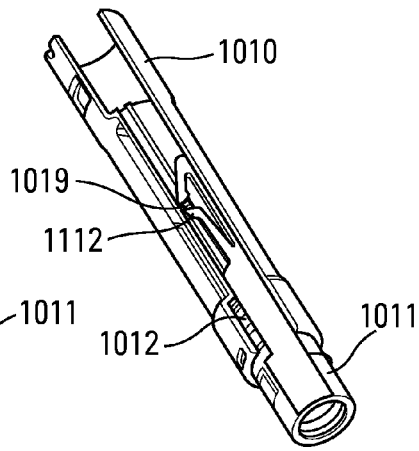
Fig. 50a　　Fig. 50b　　Fig. 50c
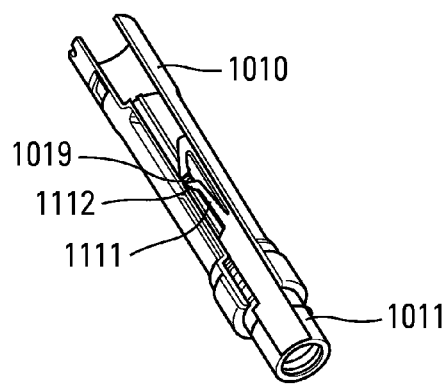
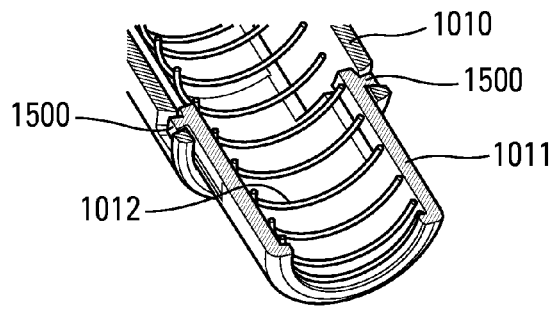
Fig. 51　　　　　　　Fig. 52

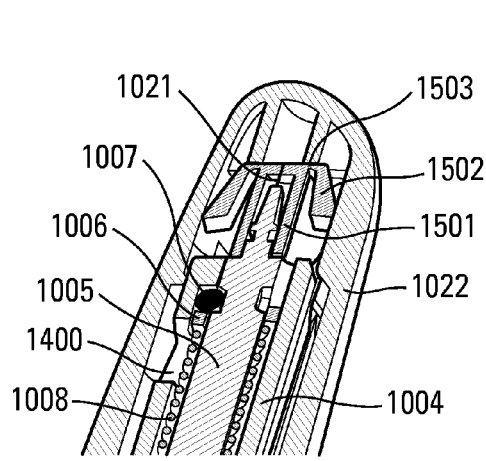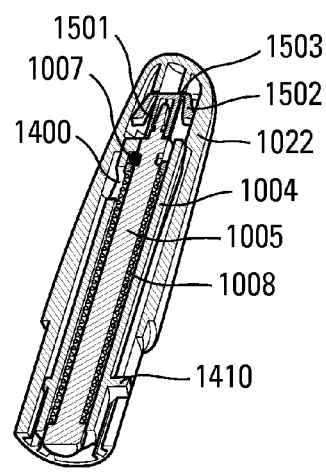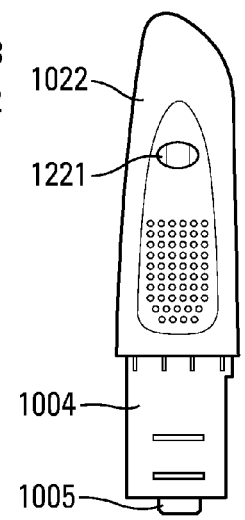
Fig. 57a  Fig. 57b  Fig. 57c
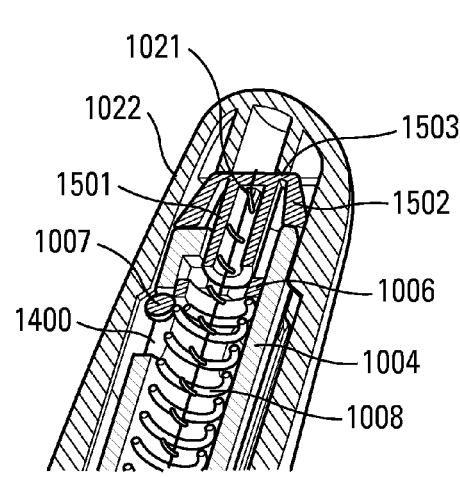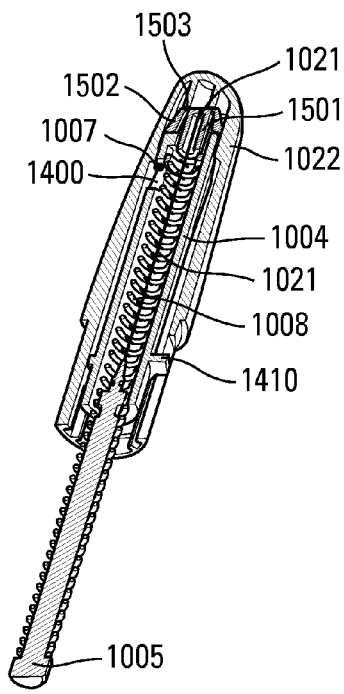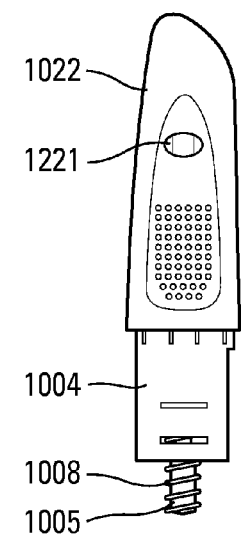
Fig. 58a  Fig. 58b  Fig. 58c

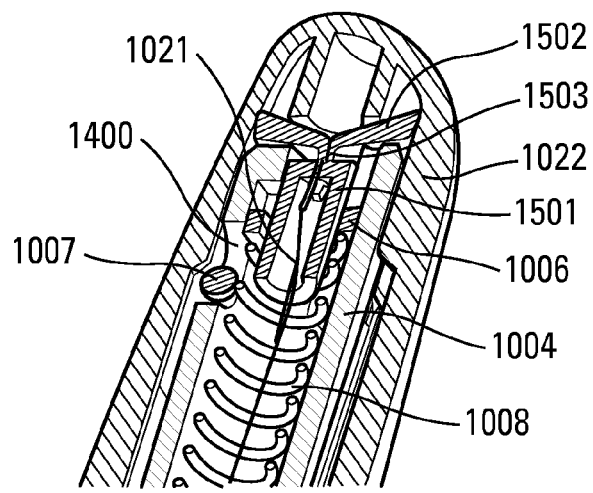
Fig. 59a
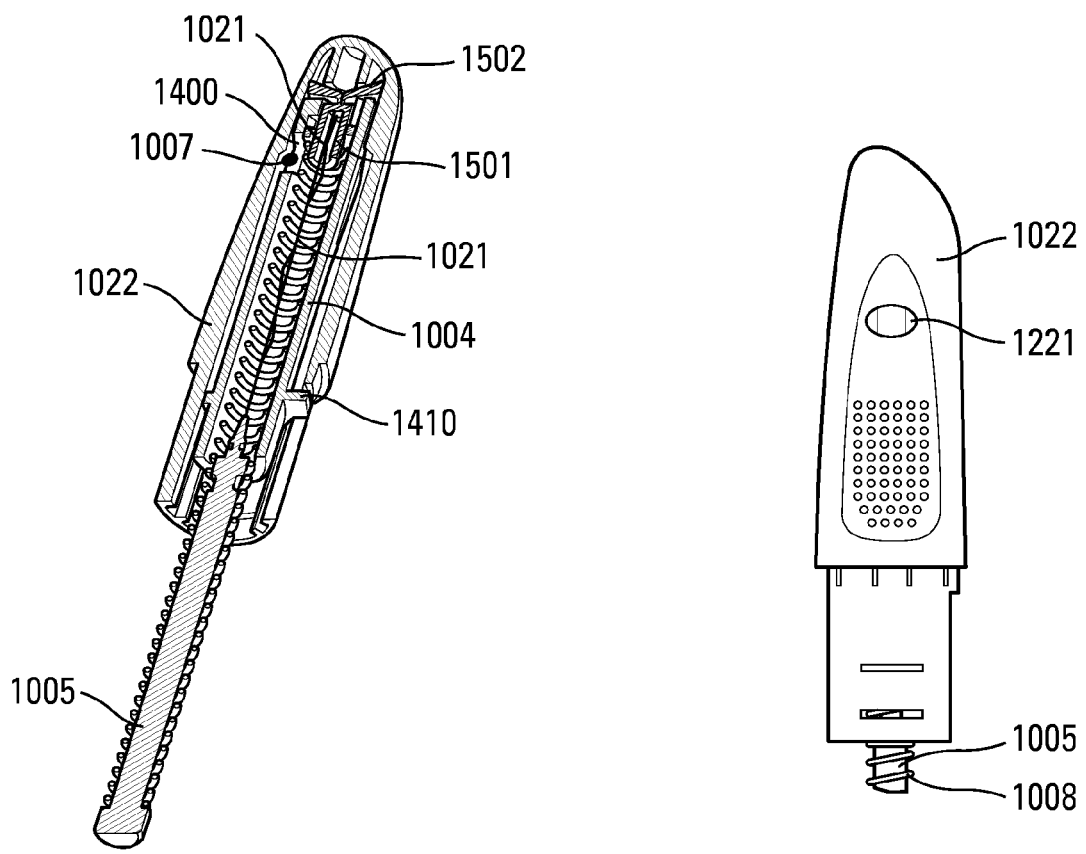
Fig. 59b
Fig. 59c

AUTOINJECTOR COMPRISING A TIME DELAY DEVICE HAVING A PLANETARY GEAR SET FOR DELAYING THE RETRACTION OF THE NEEDLE

CROSS REFERENCE TO RELATED APPLICATIONS

This application is a National Stage of International Application No. PCT/FR2013/051140 filed May 24, 2013, claiming priority based on French Patent Application Nos. 1254862, filed May 31, 2012, FR 1259116, filed Sep. 27, 2012 and FR 1352517, Mar. 21, 2013, the contents of all of which are incorporated herein by reference in their entirety.

The present invention relates to an autoinjector.

Autoinjectors are well known in the prior art. The main aim of these devices is to carry out automatic injection of the contents of a syringe inside the body of a patient. There are various systems for automating penetration of the needle into the body of the patient as well as injection of the fluid product contained in the syringe. Autoinjectors are relatively complex devices that must respond to a certain number of requirements of stresses to be reliable. The robustness of the device, its handling, and its ease of use for the user are also important elements. In addition, as the majority of these autoinjectors is single use, the cost of manufacture and assembly is also a factor to be kept in mind.

There are numerous autoinjectors on the market, all of which however have some disadvantages.

Therefore, to prevent untimely triggering of the autoinjector, for example during transport or storage, devices must comprise reliable locking means. Similarly, when a user wants to utilize the autoinjector and unlocks the device, for example by removing the cap, the device must not actuate prematurely but only when the user really wants it, that is, at the moment when he applies it to the part of the body in which he wants to carry out the injection. Now, especially when those people using the autoinjector are elderly or handicapped people, it can happen that the user drops the device just when he wants to use it. It is preferable in such a case that the autoinjector does not actuate on its own. It is therefore important to provide a reliable triggering lock. From another viewpoint, using the autoinjector should not become too difficult, which would prevent weak people from using it. It is therefore difficult to find a good compromise between the security of the locking and the ease of use and actuation of the autoinjector. It is one of the aims of the present invention to respond to this problem.

In addition, according to the volume of the fluid product distributed during injection and also as a function of its viscosity, the time needed to complete this injection can be fairly substantial, and may especially exceed several seconds. It is very important that the user not remove the device from his body before the injection is complete. It is therefore preferable for the device to comprise means for indicating reliably to the user that the injection is finished.

It is also important to ensure that the product is injected to the correct depth in the body, that is, in the right tissue. So mastering the start of injecting, to ensure there that will start only when the needle reaches its definitive pricking position, is therefore also an important aspect.

Also, to avoid any risk of injury after use of the device, the autoinjector must comprise a needle safety device which prevents the needle from being conspicuous after use of the device. This safety device must obviously also be reliable and not be released too easily. It must also be functional even if the user improperly activates the autoinjector, for example if he removes it too early from his body, prior to completion of the injection.

Another important aspect of autoinjectors, especially when the volume of fluid product is relatively large and/or when the fluid product injected is relatively viscous, is to allow the product to diffuser from the injection site for a few seconds after said injection. If the user removes the autoinjector immediately after the end of the injection, part of the product can flow back out of the body of the user, which diminishes the efficacy of the treatment. It is therefore preferable to provide that the user holds the autoinjector against his body for a few more seconds after the end of the injection. This aspect is generally resolved by existing autoinjectors by the notice of use which asks the user to count in his head for a certain number of seconds before removing the device. This is not reliable and therefore unsatisfactory, as the system then depends on the user himself who in some cases can be perturbed or weakened by what he has just done.

Documents WO2012045833, EP1743666, WO2009095701, WO2012022810, EP2399632, FR2884722, WO9632974, WO2012000832, US2008281271, WO2009040602, WO2009040604, WO2009040607, WO2010108116, WO2011048422, EP2399628, WO2008112472, WO2011101380, WO2011101382, US2005273055, FR2905273, WO2009062508, WO2009037141 and GB2463034, describe devices of the prior art.

The aim of the present invention is to provide an autoinjector that does not reproduce the abovementioned disadvantages and which responds to the different requirements and considerable restrictions for safe and reliable use of the autoinjector.

Another aim of the present invention aim is to provide an autoinjector that is reliable in use, which ensures distribution of all the fluid product at the planned site, which allows the user to determine when he must remove or when he can withdraw the autoinjector from his body after its use, which is safe and that avoids any risk of injury, and that is simple and not costly to manufacture and assemble.

The aim of the present invention is therefore to provide an autoinjector comprising a lower body receiving a tank, said tank containing fluid product and comprising a piston and a needle, such as a pre-primed syringe, said autoinjector comprising:

injection means to inject said fluid product through said needle when said needle is in an injection position; and a tank movement device for retracting said needle out of the body of the user after injection of the fluid product, a trigger, actuated by said injection means, actuating said tank movement device after injection of the fluid product so as to retract said needle;

said autoinjector comprising a retarding device adapted to delay during a predetermined time the actuation of said tank movement device by said trigger after injection of the fluid product, to delay retraction of said needle by said predetermined time after the end of injection;

said retarding device comprising an epicycloidal train having at least one stage, and advantageously four stages.

Advantageously, said trigger is stressed in rotation by a retardant spring, a locking finger arranged in said central channel blocking said rotation of said trigger.

Advantageously, said locking finger is removed from said central sleeve by said injection means, on completion of injection.

Advantageously, said injection means comprise a piston rod connected to said locking finger by a wire.

Advantageously, said trigger comprises a projection adapted to actuate said tank movement device after a predefined rotation of said trigger.

Advantageously, said projection is formed on an external inclined ramp of the trigger, said projection axially moving a control slide of the tank movement device.

Advantageously, each stage of said epicycloidal train comprises a planetary associated with at least one satellite, and advantageously three satellites.

Advantageously, each planetary comprises, on one side, at least one rod, each rod rotatably receiving a satellite, and, on the other side, a gear co-operating with the satellites of the adjacent stage.

Advantageously, said retarding device includes an upper body provided with a central sleeve and with a gear on its lateral internal surface, said gear co-operating with said satellites.

Advantageously, said epicycloidal train comprises at least two planetaries, a first planetary being driven in rotation by said trigger, the satellites of said first planetary driving said second planetary in rotation, the rotation of said second planetary being demultiplied so as to brake the rotation of the trigger.

These characteristics and advantages and others of the present invention emerge more clearly from the following detailed description, given in reference to the attached drawings, given by way of non-limiting examples, and in which:

FIG. 4 is a detailed view showing the actuating sleeve in the position of FIG. 3a;

FIGS. 5 and 6 are detailed views in transversal section according to two different sectional planes showing the actuating sleeve in the position of FIG. 4;

FIGS. 7 and 8 are partially cut schematic views in perspective illustrating the actuating sleeve in the position of FIGS. 5 and 6;

FIGS. 33 to 35 are partially cut schematic views in perspective of the movement mechanism of FIG. 32, prior to actuation, according to three different orientations;

FIGS. 36 and 37 are views similar to FIGS. 33 and 35, during actuation of the movement mechanism;

FIGS. 38 to 41 are partially cut partial schematic views in perspective of the movement mechanism of FIG. 32, when the needle of the syringe has reached its injection position in the body of the user;

FIGS. 42 and 43 are schematic views of the movement mechanism of FIG. 32 at the start of retraction initiated by the retarder;

FIG. 44 is a schematic view of the movement mechanism of FIG. 32 at the start of retraction initiated by the actuating sleeve;

FIGS. 48a to 48e are schematic views in transversal section illustrating the different sequences of use of the autoinjector of FIG. 47;

FIGS. 49a and 49b are schematic views in perspective illustrating the lower body and the actuating sleeve of the autoinjector of FIG. 47;

Figure 47:
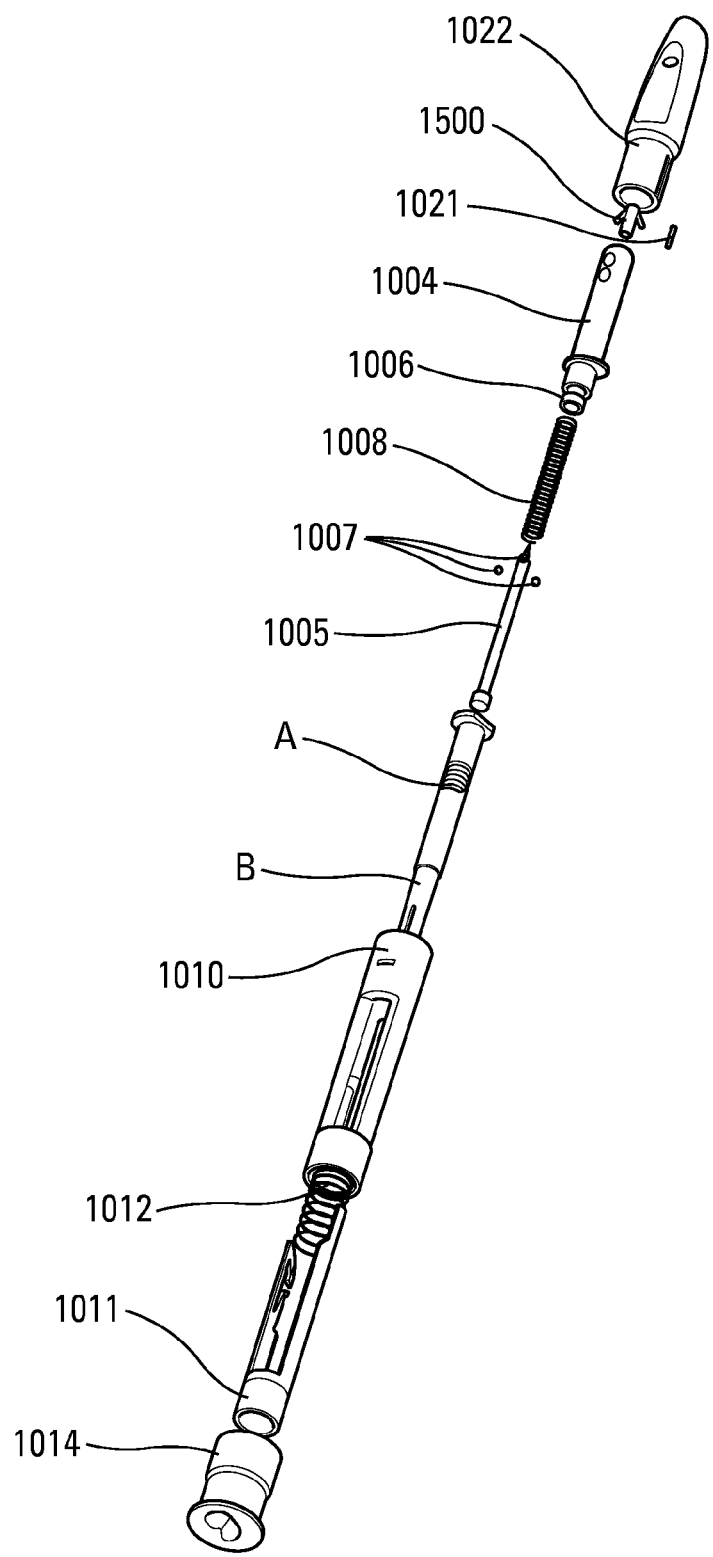
FIG. 47 is an exploded schematic view in perspective of the components of an autoinjector, according to an advantageous second embodiment.
Figures 53A, 53B, 54A, 54B:
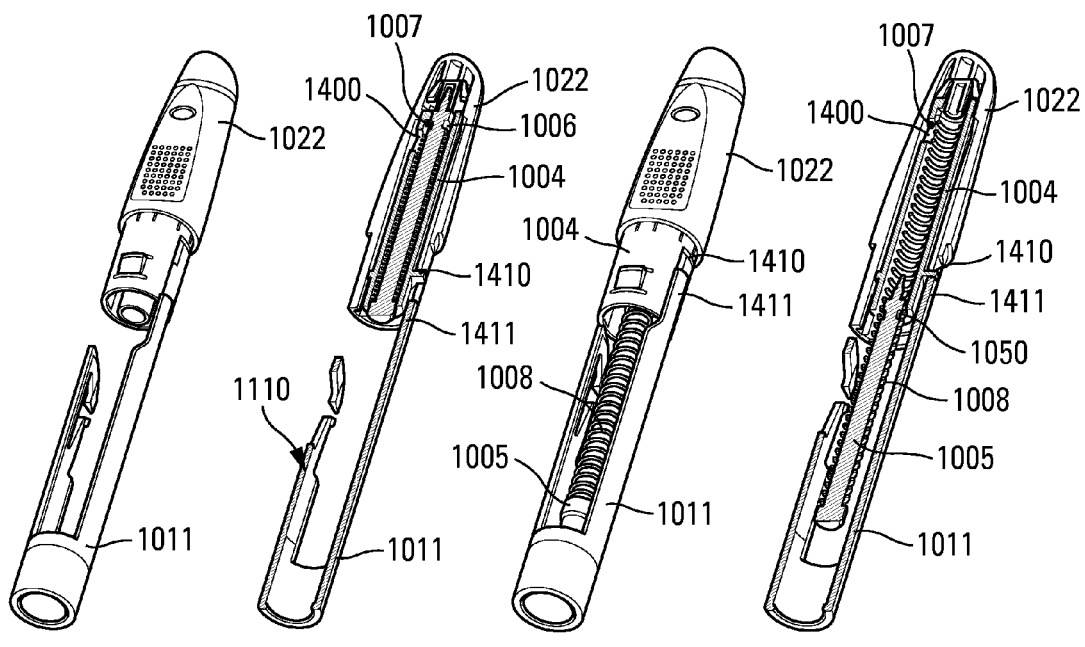
Figures 55, 56:
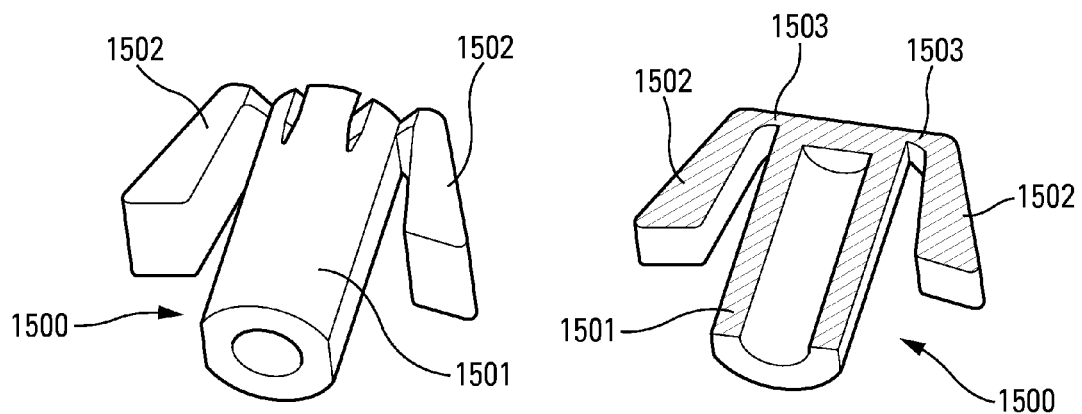
Figure 60:
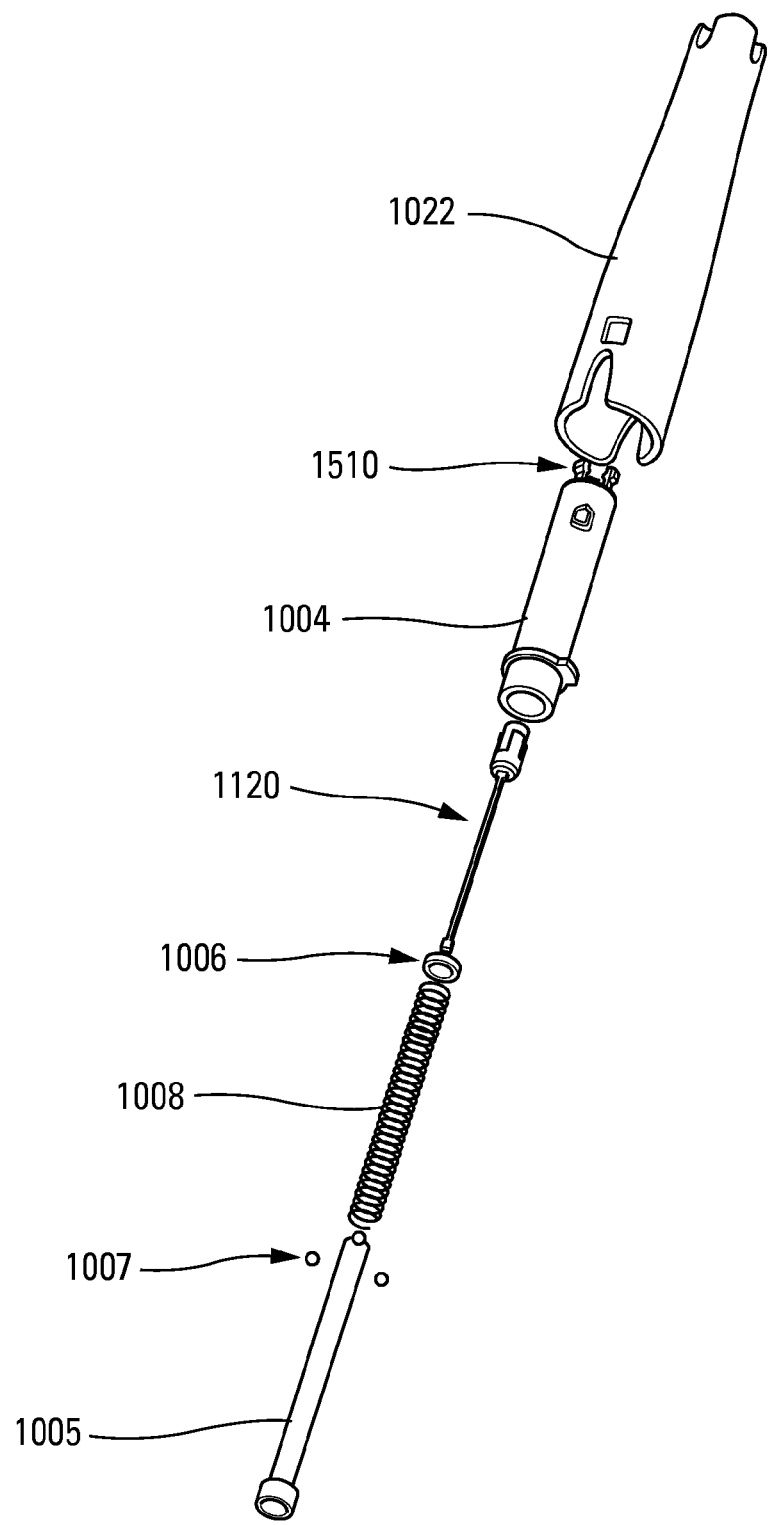
Figures 61, 62, 63A, 63B:
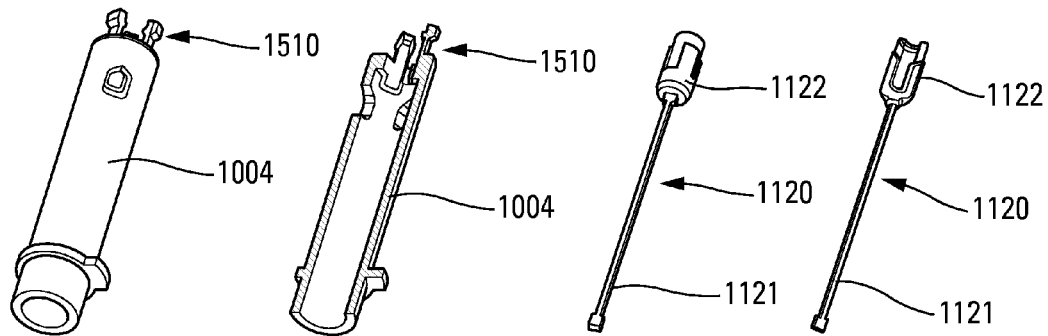
Figures 64A, 64B, 64C:
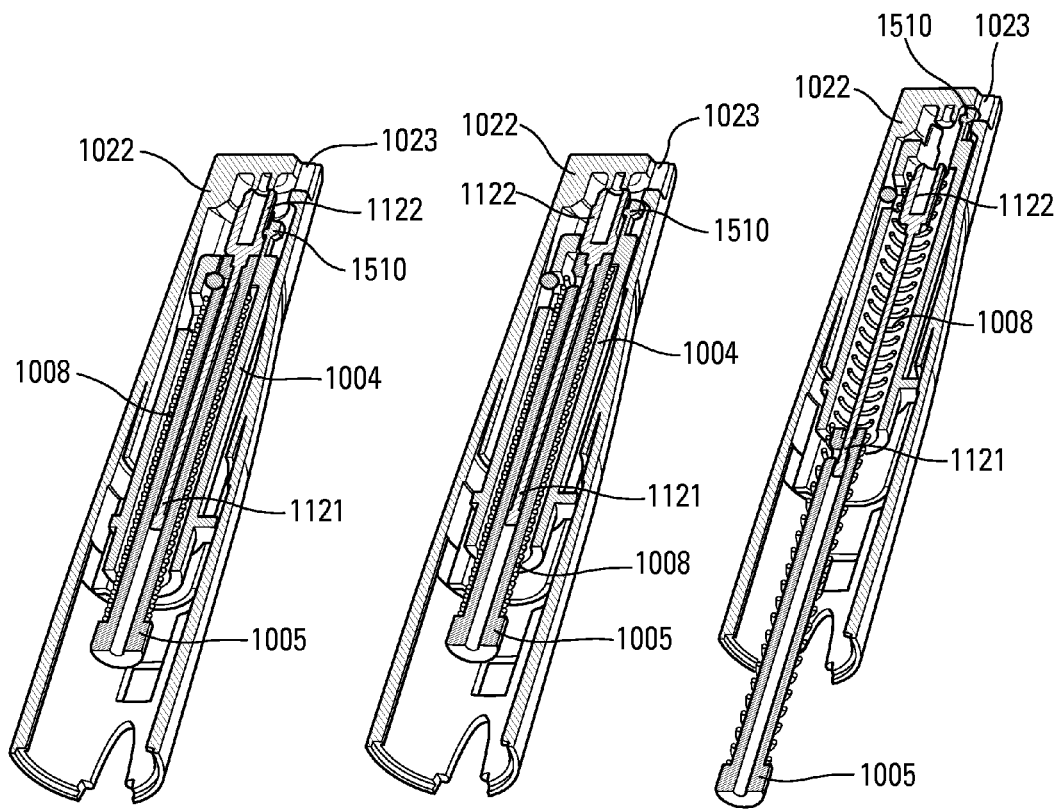
Figure 65:
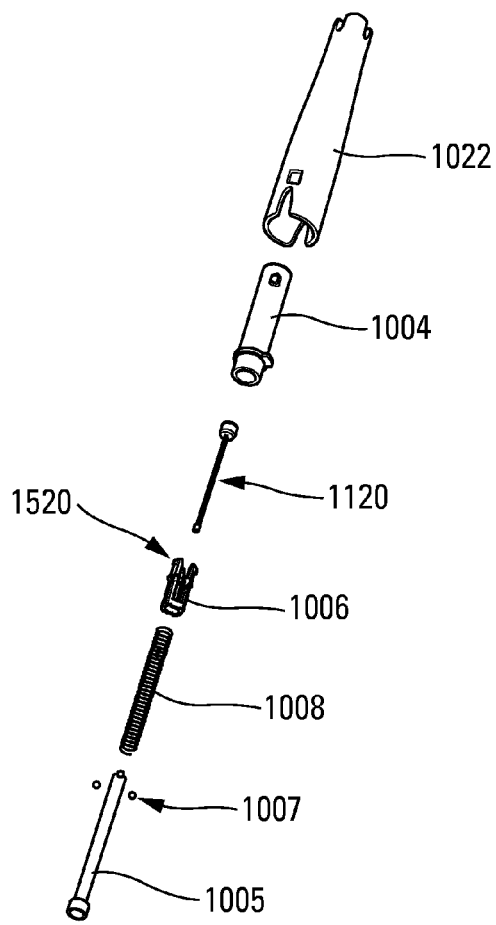
Figures 66A, 66B, 67A, 67B:
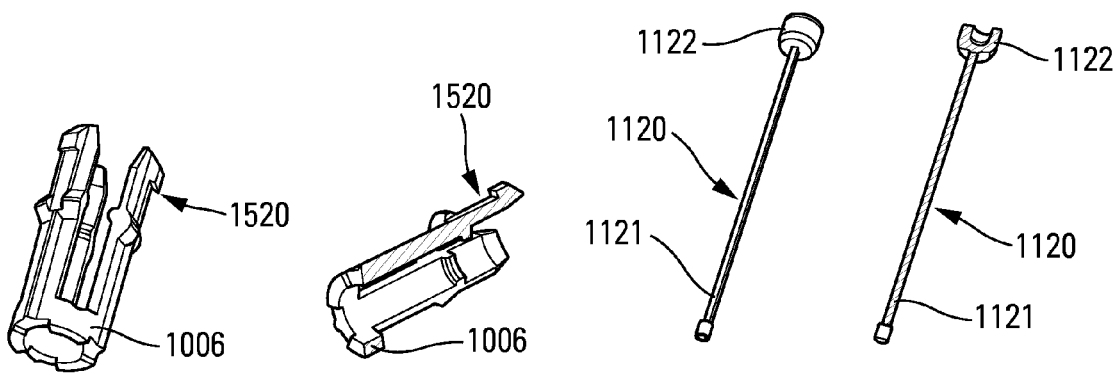
Figures 68A, 68B, 68C:
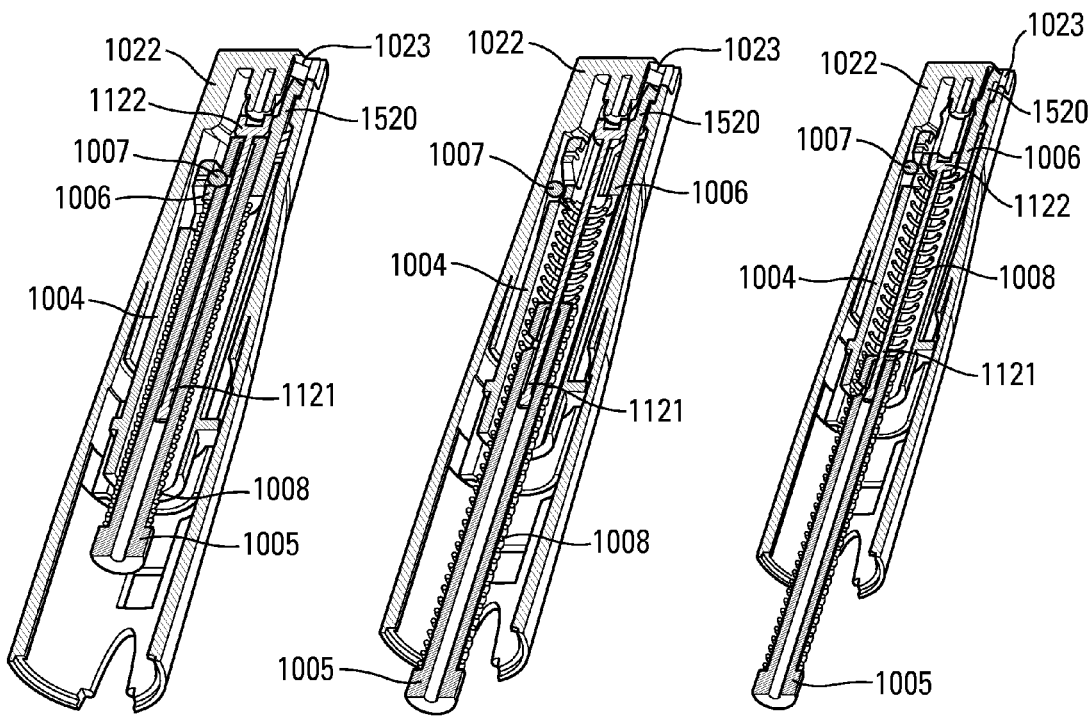
Figures 69, 70, 71:
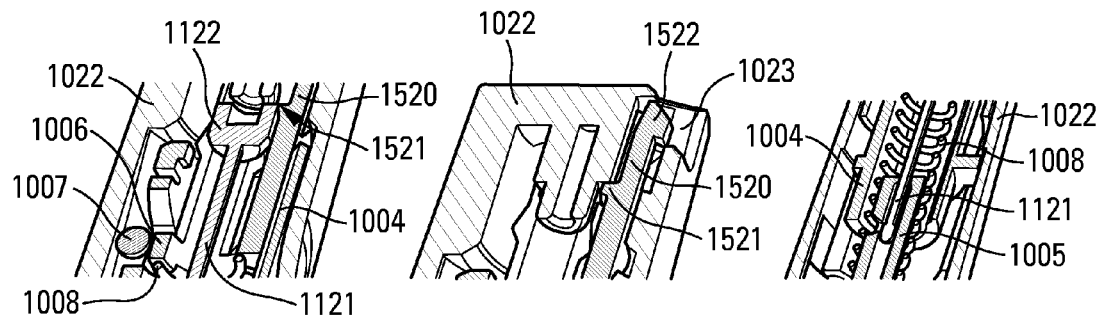
Figure 72:
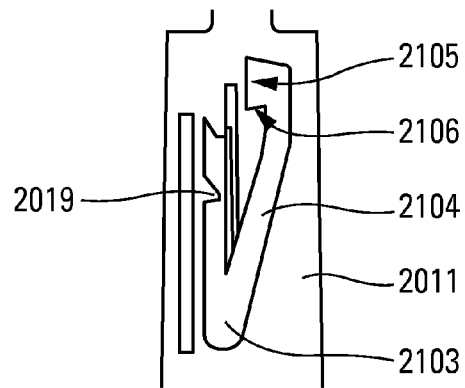
Figure 73:
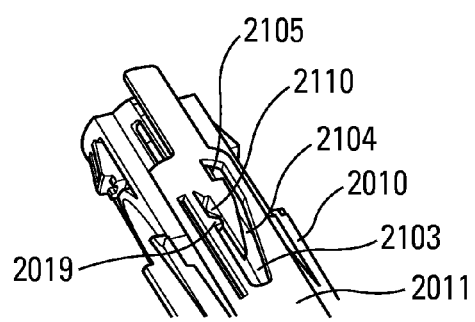

FIGS. 50a, 50b and 50c schematically illustrate the cooperation between the actuating sleeve and the lower body of the autoinjector of FIG. 47, respectively in position prior to actuation, after actuation but prior to injection and after injection;

FIG. 51 is a view similar to that of FIG. 50a, illustrating a variant embodiment;

FIG. 52 is a detailed cut enlarged view in perspective, showing a variant of the actuating sleeve with scored bridges;

FIGS. 53a and 53b illustrate schematic views of the autoinjector prior to injection;

FIGS. 54a and 54b are views similar to FIGS. 53a and 53b, after injection;

FIG. 55 is a schematic view in perspective of a sound and/or tactile indication device according to an advantageous variant;

FIG. 56 is a view similar to FIG. 55, partially in section;

FIGS. 57a, 57b and 57c show the autoinjector prior to injection;

FIGS. 58a, 58b and 58c show the autoinjector after injection but prior to actuation of the sound and/or tactile indication device;

FIGS. 59a, 59b and 59c show the autoinjector after injection and after actuation of the sound and/or tactile indication device;

FIG. 60 is a schematic view in perspective exploded illustrating a variant embodiment of the sound and/or tactile indication device;

FIGS. 61 and 62 are schematic views of the control sleeve of the sound and/or tactile indication device of FIG. 61;

FIGS. 63a and 63b are schematic views of the key of the sound and/or tactile indication device of FIG. 61;

FIGS. 64a, 64b and 64c are schematic views of the autoinjector of FIG. 60, respectively before unlocking of the injection lock, after unlocking of the injection lock and on completion of injection, illustrating the sound and/or tactile indication device of FIG. 61;

FIG. 65 shows another variant embodiment of the sound and/or tactile indication device;

FIGS. 66a and 66b are schematic views of the support pellet of the sound and/or tactile indication device of FIG. 65;

FIGS. 67a and 67b are schematic views of the key of the sound and/or tactile indication device of FIG. 65;

FIGS. 68a, 68b and 68c are views similar to FIGS. 64a, 64b and 64c, illustrating the sound and/or tactile indication device of FIG. 65;

FIGS. 69, 70 and 71 are detailed views of FIGS. 68b and 68c;

FIG. 72 schematically shows a variant embodiment of the actuating sleeve;

FIG. 73 shows another view of the variant embodiment of FIG. 72; and

Figures 74A, 74B, 74C:
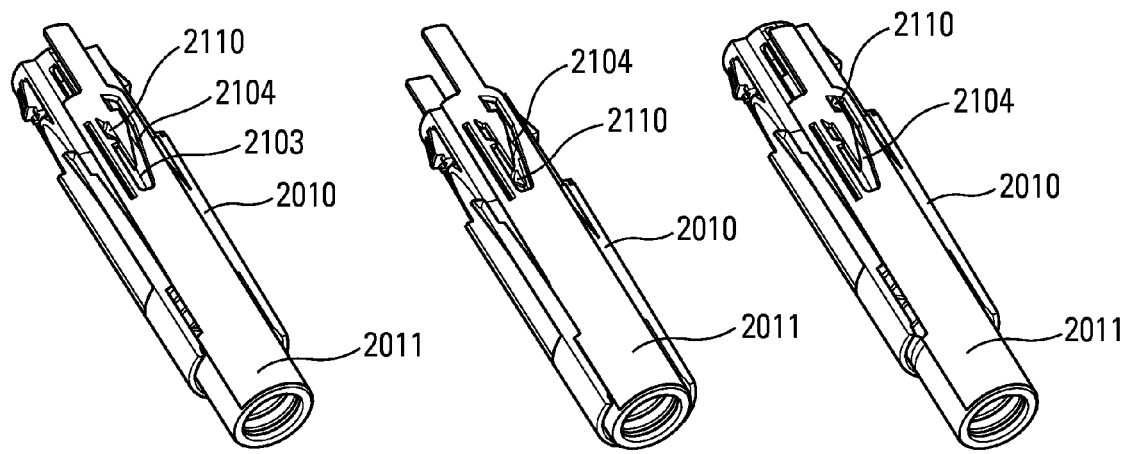

FIGS. 74a, 74b and 74c are views similar to FIGS. 50a, 50b and 50c, illustrating the variant embodiment of the actuating sleeve of FIGS. 71 and 72.

The autoinjector is described hereinbelow in reference to diverse variants of two advantageous embodiments thereof. A first embodiment is shown in FIGS. 1 to 46 and a second embodiment is shown in FIGS. 47 to 74c. It is however to be noted that these autoinjectors, which are complex devices, comprise several modules for carrying out several functions. These diverse modules can be used separately and independently of each other, without necessarily being combined with other modules, and could especially be used in autoinjectors of form different to that shown in the drawings.

Figure 1:
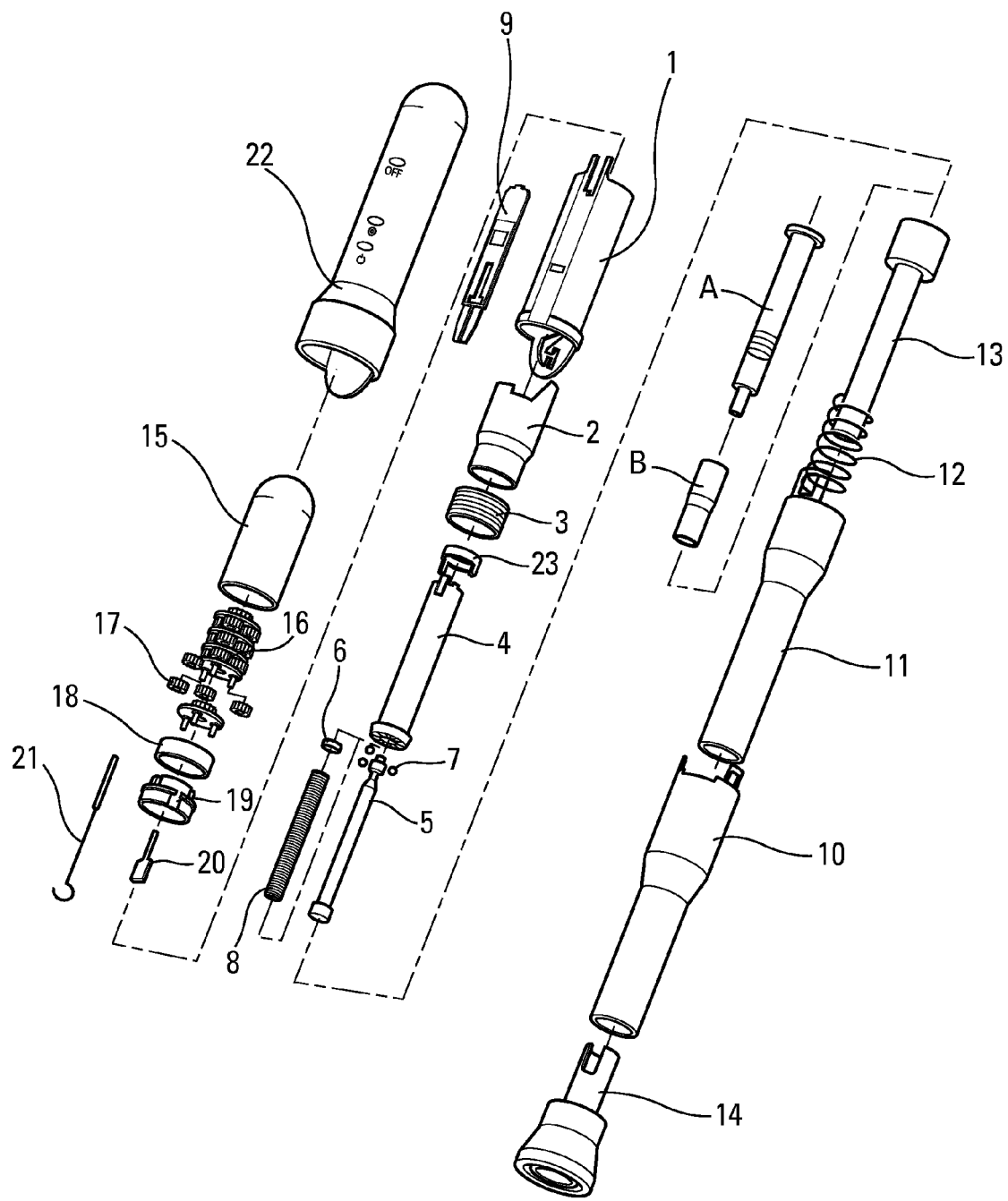
FIG. 1 is a schematic exploded view in perspective of the components of an autoinjector, according to a first advantageous embodiment.
Figure 2:
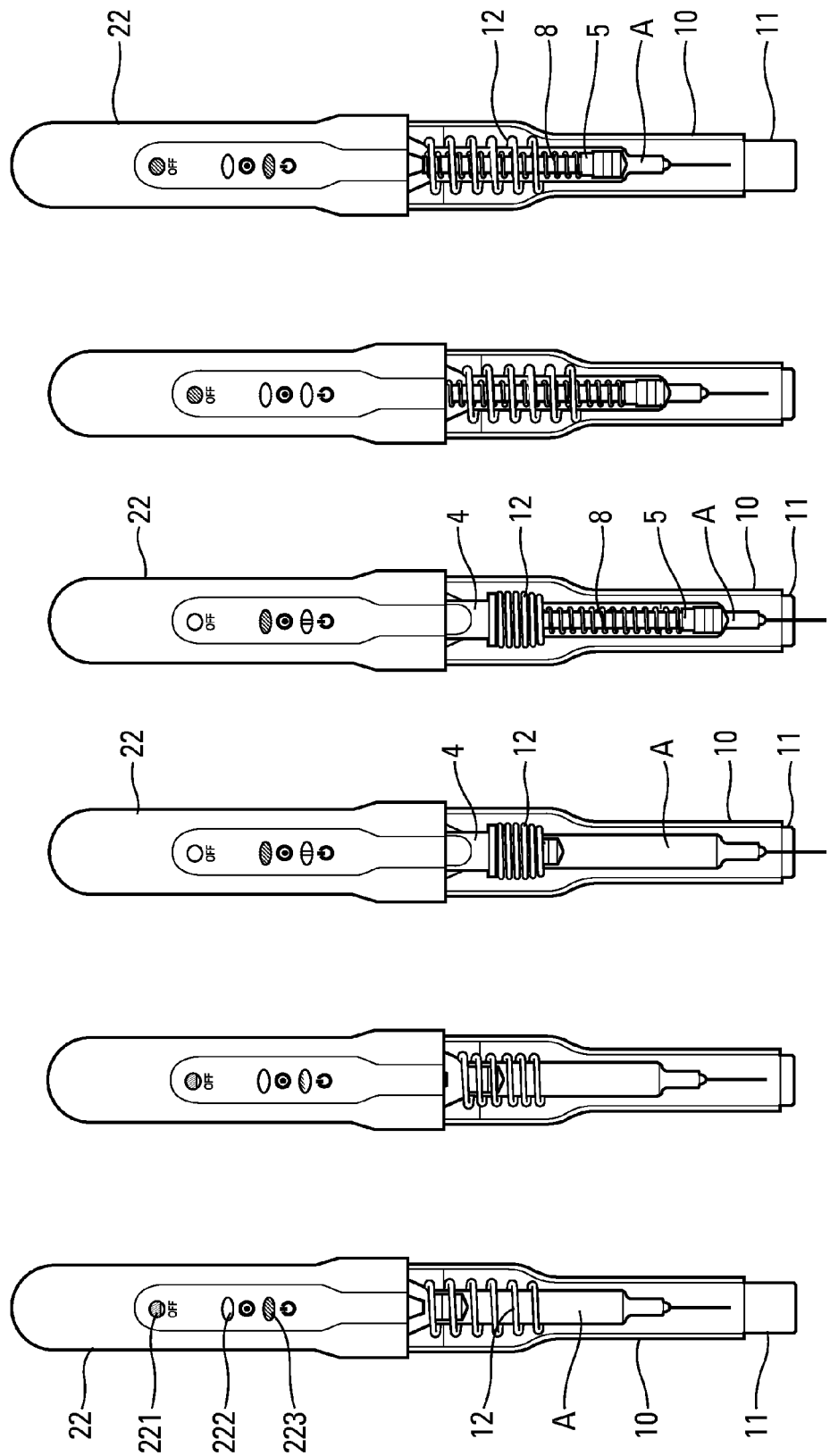
FIGS. 2a to 2f are schematic views in transversal section illustrating the different sequences of use of the autoinjector of FIG. 1.
Figure 3:
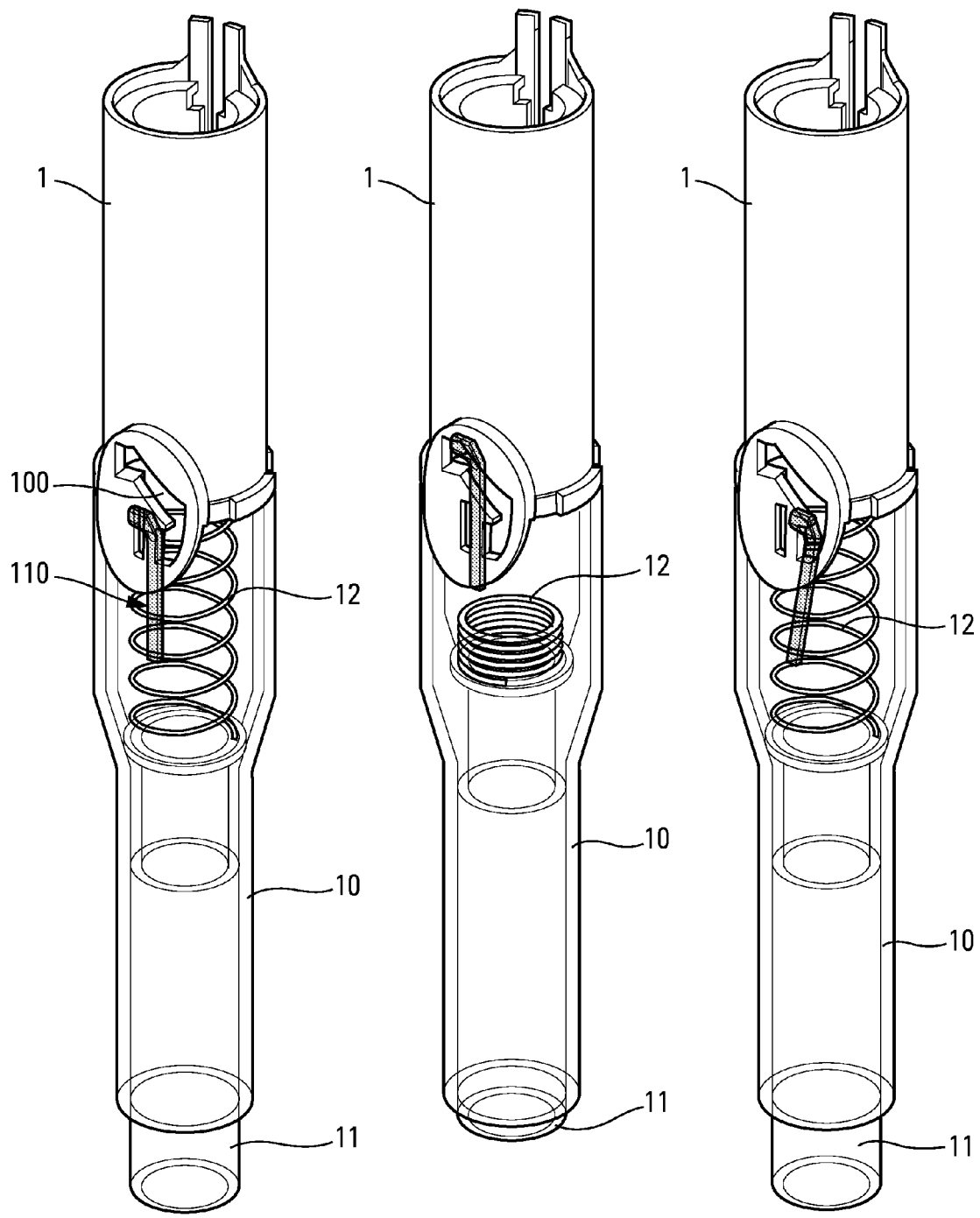
FIGS. 3a to 3c illustrate more precisely three different stages of an advantageous actuating sleeve, respectively before, during and after use.
Figures 9, 10, 11, 12:
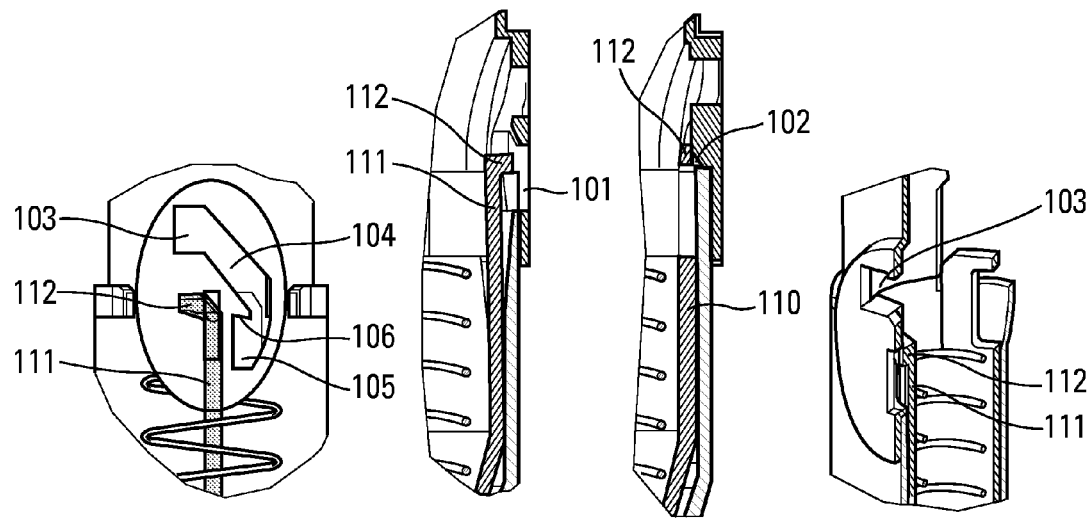
FIG. 9 is a view similar to that of FIG. 4, at the start of actuation of the autoinjector, during the pricking phase.
FIGS. 10 to 11 are views similar to FIGS. 5 and 6, in the position of FIG. 9.
FIG. 12 is a view similar to that of FIG. 8, in the position of FIGS. 10 and 11.

In reference to FIG. 1, the different components of the autoinjector, according to a first advantageous embodiment, are shown exploded. In this first embodiment, and in the order of the reference numerals, the autoinjector comprises a central body 1, a control ring 2, a pricking spring 3, a control sleeve 4, a piston rod 5, a pellet support 6, three blockage elements 7, here in the form of balls, an injection spring 8, a control slide 9, a lower body 10, an actuating sleeve 11, a spring 12 of the actuating sleeve, a tank housing 13, a cap 14, an upper body 15, a plurality of planetaries 16, a plurality of satellites 17, a retardant spring 18, a trigger 19, a locking finger 20, a wire 21, an external shell 22 and a blocking ring 23. All these elements form part of the embodiment described, but all are not indispensable to the operation of the autoinjector, as is described more precisely hereinbelow.

The cap 14 especially locks the autoinjector during transport and storage. As this cap is assembled on the lower body 10, it prevents any actuation of the actuating sleeve 11, and therefore any triggering of the autoinjector.

A tank A can be inserted into said autoinjector. This tank contains fluid product, and comprises a piston and a needle. The piston is adapted to shift in said tank to inject the fluid product through said needle. The present description will be given in reference to a syringe A, which can be any type. More generally, it is understood that the term "syringe" in the present description covers any type of tank linked to a needle.

Preferably, the syringe A is a pre-filled syringe. It advantageously comprises a needle cap B which protects and isolates the needle prior to use of the autoinjector. Advantageously, this needle cap B is removed automatically at the moment when the cap 14 is withdrawn from the lower body 10.

FIGS. 2a to 2f illustrate the sequences of the use of the autoinjector of FIG. 1.

In FIG. 2a, the autoinjector is in the rest position prior to use, the cap 14 having been removed.

When the user wants to use the autoinjector, he takes the device, for example at the level of the external shell 22 and presses the actuating sleeve 11, which in a first projected position projects out of the lower body 10, against the part of the body where he wants to carry out the injection. In FIG. 2b, it is evident that pressure exerted by the user on the actuating sleeve 11 causes the latter to slide towards the interior of the lower body 10, with the effect of compression of the spring of the actuating sleeve 12.

When the actuating sleeve 11 reaches its actuation position, which is its end position inside the lower body 10, it causes triggering of the pricking lock and therefore movement of the control sleeve 4 in the lower body 10 under the effect of the pricking spring 3, consequently with movement of the syringe A in the lower body 10 and therefore insertion of the needle of the syringe in the body of the user, as is evident in FIG. 2c.

When the needle reaches its injection position with complete insertion of the needle, the injection phase is triggered, which is shown in FIGS. 2c and 2d. It is noted that the piston rod 5 slides inside the syringe A by pushing the piston thereof under the effect of the injection spring 8. The product is therefore distributed.

On completion of the injection, and with optionally a certain delay or time offset, as is described below, the autoinjector provides retraction of the syringe A. The needle is therefore retracted out of the body of the user towards the interior of the autoinjector, as shown in FIG. 2e.

On completion of retraction, the actuating sleeve 11 is again moved out of the lower body 10 towards a second projected position, under the effect of the spring 12 of the actuating sleeve, with locking of said actuating sleeve 11, which ensures absolute safety for the user and avoids any risk injury with the needle after use of the device. It is evident that the first and second projected positions of the actuating sleeve, which in the example shown are different positions, could optionally be identical.

An advantageous actuating sleeve is described in more detail hereinbelow in reference to FIGS. 3a to 18.

Said actuating sleeve 11 comprises a flexible foot 110 that has double flexibility. It is on the one hand flexible radially that is, it deforms towards the interior of the actuating sleeve 11. It is then also flexible laterally that is, it deforms in the peripheral direction of the actuating sleeve 11. An actuating sleeve 11 provided with such a flexible foot is simple to mold, which is favorable from the point of view of manufacturing costs. The flexible foot 110 advantageously comprises a rod part 111 that is flexible and which terminates in a head part 112. Said flexible foot 110 is adapted to deform on the one hand radially and on the other hand laterally relative to said central body 1 when said actuating sleeve 11 is moved from its first projected position towards its actuation position then from its return actuation position towards its second projected position. Preferably, said flexible foot 110 is deformed radially when said actuating sleeve 11 is moved from its first projected position, prior to actuation, towards its actuation position, and said flexible foot is deformed laterally when said actuating sleeve 11 is moved from its actuation position towards its second projected position, at the end of use. This is the variant that is shown in the figures.

FIGS. 3a, 3b and 3c are three partial schematic views in perspective that show the end positions of the actuating sleeve 11, specifically in FIG. 3a the first projected position at rest prior to actuation, in FIG. 3b the actuation position in which the actuating sleeve 11 has been inserted to the maximum inside the lower body 10, and in FIG. 3c the second projected position with the actuating sleeve 11 locked relative to the lower body 10, at the end of use.

It is noted that the central body 1 comprises cutouts forming grooves and shoulders that are detailed hereinbelow. The central body 1 is fixed to the lower body 10 and the actuating sleeve 11 is arranged to slide inside said lower body 10.

The central body 1 comprises a substantially axial first groove 101, and an opening 103, separate from said first groove 101 but arranged in the axial extension of said first groove 101. Said central body 1 also comprises a radial cam 102 arranged between said first groove 101 and said opening 103. As evident especially in FIGS. 6 and 7, said radial cam 102 can be formed by inclined radial thickening of the wall of the central body 1, said thickening being formed at the axial end of the first groove 101. Said radial cam 102 cooperates with said head 112 of said flexible foot 110 to radially deform said flexible foot 110 and allow said head 112 to move from said first groove 10 to said opening 103 during movement of the actuating sleeve 11 towards its actuation position.

Said central body 1 comprises a final reception zone 105 offset axially and laterally relative to said opening 103. As evident in the figures, this final reception zone 105 is arranged axially around the level of said first groove 101. The opening 103 is connected to said final reception zone 105 by a laterally inclined groove 104. An axial shoulder 106 is provided between said final reception zone 105 and said inclined groove 104. Therefore, when said actuating sleeve 11 returns from its actuation position towards its second projected position, said head 112 of the flexible foot 110 slides in said laterally inclined groove 104, laterally deforming said flexible foot 110. When said actuating sleeve 11 reaches its second projected position, after use, said head 112 clips in under said axial shoulder 106, locking said actuating sleeve 11 relative to said central body 1 and relative to the lower body 10. From this locked position, said actuating sleeve can no longer be moved in the direction of its actuation position, due to the stop formed between the head 112 of the flexible foot 110 and the axial shoulder 106.

FIGS. 4 to 8 represent the start position, that is, at the moment when the user will commence using the autoinjector. It is evident in these figures that the head 112 is arranged in said groove axial 101 of the central body 1. When the actuating sleeve 11 slides towards the interior of the lower body 10, said head 112 of the flexible foot 110 will slide inside said groove 101 of the central body. When the head 112 reaches the axial end of the first groove 101, said radial cam 102 will cooperate with said head 112. This radial cam 102 will therefore deform the flexible foot 110, and especially its rod part 111, radially towards the interior in the direction of its longitudinal central axis.

Figures 13, 14, 15, 16:
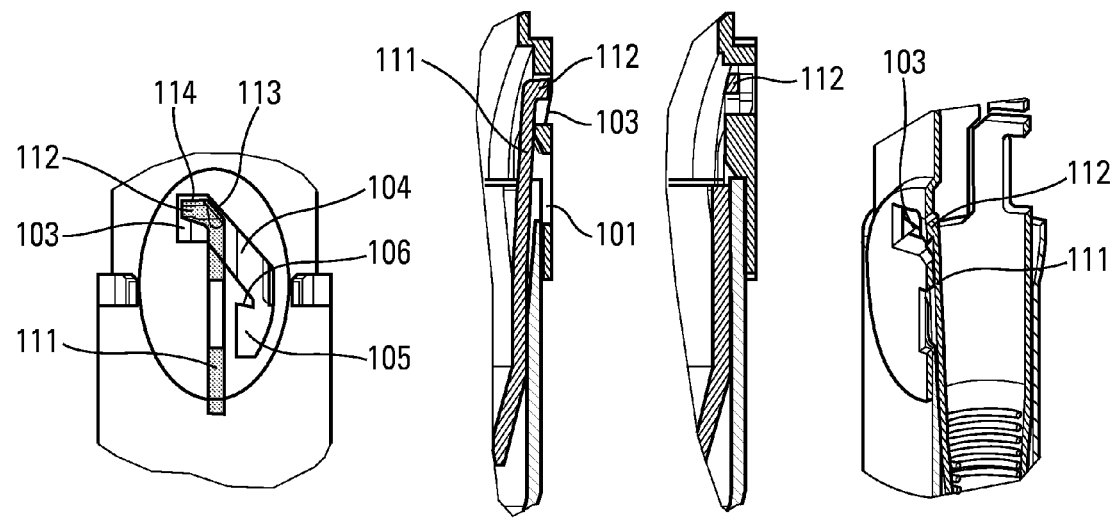
FIG. 13 is a view similar to that of FIGS. 4 and 9 during actuation, in the injection phase.
FIGS. 14 and 15 are views similar to those of FIGS. 10 and 11 illustrating the position of FIG. 13.
FIG. 16 is a view similar to that of FIG. 12, illustrating the position of FIGS. 14 and 15.
Figure 17:
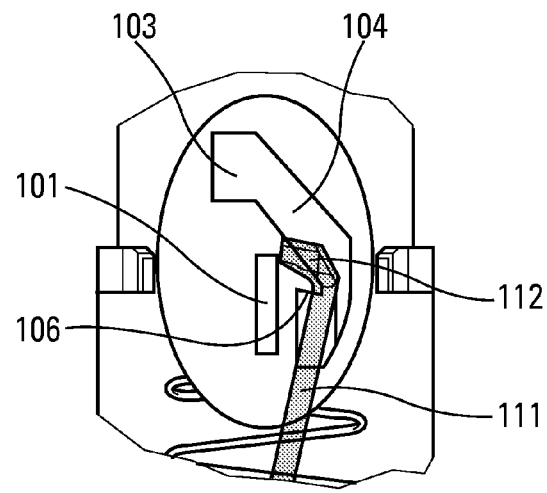
FIG. 17 is a view similar to that of FIG. 13, at the end of actuation, when the user removes the autoinjector from the injection site.
Figure 18:
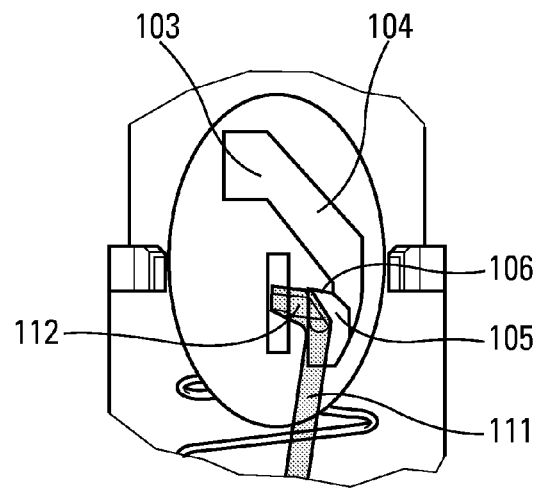
FIG. 18 is a view similar to that of FIG. 17, when the actuating sleeve is locked.

FIGS. 9 to 12 illustrate the position in which the flexible foot 110 is radially deformed. As evident especially in FIG. 11, after this radial deformation the head 112 of the flexible foot 110 will continue to move axially over an additional distance to reach said opening 103. The actuating sleeve 11 reaches its actuation position, as shown in FIG. 13.

In this actuation position, the flexible foot 110 returns elastically to its radially non-deformed position. The head 112 of the flexible foot 110 returns inside said opening 103, as is evident in FIG. 14.

The radial deformation of the flexible foot 110, necessary to move the actuating sleeve from its first projected position towards its actuation position, generates some resistance. Combined with the compression force of the spring 12, this resistance obliges the user to exert at least some predetermined force to perform movement of the actuating sleeve 11 inside the lower body 10. This avoids any risk of accidental or unwanted actuation after the cap 14 is removed. Actuation takes place only if the user exerts said predetermined force on the actuating sleeve 11. This force threshold also creates some precompression in the hand of the user, the effect of which is that movement of the actuating sleeve 11 towards its actuation position is ensured when this threshold is reached.

When the actuating sleeve 11 reaches its actuation position, that is, in the position of FIGS. 13 to 16, the spring 12 of the actuating sleeve has been compressed and the pricking lock is triggered by said actuating sleeve 11, as is described in more detail later, which causes movement of the syringe A inside the lower body 10 and therefore pricking of the needle in the body of the user. Throughout this pricking phase and during the injection phase which follows said pricking phase, the actuating sleeve 11 does not move relative to the lower body 10, since the user maintains his pressure on the part of the body in which he is injecting.

At the end of use, when the user is going to remove the autoinjector from his body, the spring 12 of the actuating sleeve 11 will stress said actuating sleeve 11 to return from its actuation position towards its second projected position, as is shown in FIG. 3c. During this axial return deformation of the actuating sleeve 11 in the lower body 10, the head 112 of the flexible foot 110 will cooperate with the inclined groove 104 as is evident in FIGS. 17 and 18. This will cause elastic deformation of the flexible foot 110, and especially of its rod part 111, to the extent where the actuating sleeve 11 will slide axially, the head 112 sliding in said inclined groove 104 laterally deforming said flexible foot 110 as clearly evident in FIG. 17. This inclined groove 104 terminates in a final reception zone 105 provided with an axial shoulder 106. At the end of the return path of the actuating sleeve 11, the head 112 of the flexible foot 110 will penetrate this final reception zone 105 and the upper edge 114 of the head 112 will cooperate with the axial shoulder 106, which will block the actuating sleeve 11 relative to the lower body 10. The actuating sleeve 11 can no longer slide axially towards the interior of the lower body 10, and the safety device is then in the final locked position. Therefore, the needle is fully protected after use and the user can no longer utilize the autoinjector or injure himself with the needle.

Of course, the forms of the grooves, their dimensions and their inclinations can be modified as a function of the preferred needs and characteristics for the needle safety device.

The actuating sleeve described above is particularly effective and reliable, and is robust and easy and therefore inexpensive to mold.

FIGS. 32 to 46 describe more particularly the device for movement of the syringe in the lower body 10. This device for movement ensures on the one hand the pricking, that is, insertion of the needle in the body of the user, and on the other hand retraction of the needle after injection.

As seen previously, at the start of actuation, the syringe A is moved axially in said lower body 10 to perform insertion of the needle in the body of the user. After injection of the fluid product in the body of the user, and optionally after some delay provided by the retarding device described above, the syringe A is again moved in the other direction inside the lower body 10 to be retracted and automatically withdraw the needle from the body of the user. In this way, when the user removes the autoinjector from his body, the needle no longer projects but instead is retracted inside said autoinjector.

To perform these reciprocal movements of the syringe A in the lower body 10, a control ring 2 is provided which cooperates with the control sleeve 4, with the control slide 9 and with the actuating sleeve 11. In addition, the trigger 19 intervenes to perform retraction of the syringe inside the body, as is explained hereinbelow.

FIGS. 33 to 35 illustrate the start position before the syringe is moved for pricking. It is noted that the control ring 2 is stressed in rotation by the pricking spring 3, which here is a spring acting in torsion. Such a torsion spring performs painless pricking.

In this initial position of FIGS. 33 to 35, rotation of the control ring 2 is prevented by a projection 91 of the control slide 9, as is more clearly evident in FIG. 35.

When the actuating sleeve 11 arrives in its end position inside the lower body 10, as shown in FIG. 3b, a shoulder 118 of said actuating sleeve 11 will cooperate with a shoulder 92 of the control slide 9 to axially move said control slide 9 upwards in FIG. 36. This axial deformation of the control slide 9 will release the rotation of the control ring 2 that will be able to turn under the effect of its loaded pricking spring 3.

The control ring 2 comprises three inclined profiles 24, 25, 26 similar to ramps, whereof the functions are explained hereinbelow.

The control ring 2 comprises a first inclined internal profile 24, such as a ramp, which will cooperate with a projection 44 of the control sleeve 4. Therefore, rotation of the ring 2 will progressively axially move said control sleeve 4. This control sleeve 4 cooperates with the syringe housing 13 that receives the syringe, and movement of the control sleeve moves the syringe A in the lower body 10 to perform pricking of the needle.

FIG. 39 illustrates the position in which the needle is fully inserted, with the first inclined profile 24 which cooperates with the projection 44 of the control sleeve 4.

During movement of the control sleeve 4 and therefore insertion of the needle into the body of the user, the projection 91 of the control slide is also in contact with an external inclined profile 25 of the ring 2, such as an external ramp, which will cause added axial deformation of said control slide 9 relative to the actuating sleeve 11. This will move the control slide 9 in the same direction as the actuating sleeve 11 during pricking. Because of this, the projection 92 of the control slide 9 comes close to an upper projection 119 of the actuating sleeve 11, and the projection 95 of the control slide 9 comes close to a projection 191 of the trigger 19, as is evident in FIG. 44.

The first internal inclined ramp 24 which cooperates with the projection 44 of the control sleeve 4 advantageously comprises a flat section 241, that is, a non-inclined portion, evident in FIG. 41. This flat section 241 has a very important function since it ensures that the start of the injection will occur only after the total end of insertion of the needle into the body of the user. Whereas for many autoinjectors it is necessary to commence the injection slightly before the needle reaches its final insertion point, for reasons of manufacturing tolerance the flat section 241 on the ramp 24 avoids this phenomenon. In fact, while the ring 2 has already completely moved the control sleeve 4 axially and therefore has completed total insertion of the needle of the syringe in the body of the user, it is necessary for the ring 2 to turn further on the arc of a circle formed by said flat section, for example around 30°, to trigger the injection lock. Therefore, the blocking ring 23 of the injection lock is moved from its blocking position only after the extra rotation of the ring 2 on the arc of a circle formed by said flat section 241. During this extra rotation, there is no axial deformation of the control sleeve 4, and therefore of the syringe A, since the flat section 241 is not inclined. Even with manufacturing tolerances, this guarantees that insertion is finished before injection commences. In line with this, during this extra rotation of the control ring 2 a second internal inclined profile 26, such as a ramp, of the control ring 2 will cooperate with a projection 235 of the blocking ring 23 of the injection lock and move the latter from its blocking position to release the injection, when the control ring 2 arrives at the end of its extra rotation. This is also evident in FIG. 41. Advantageously, the control ring 2 comprises three second internal inclined profiles 26 arranged at 120° to each other, and the blocking ring 23 comprises three projections 235 also arranged at 120° to each other, a respective projection 235 cooperating with a respective second internal inclined profile 26.

When the injection is triggered by the blocking ring 23, the rotation of the control ring 2 is again blocked by the control slide 9.

With the control slide 9 in the position of FIG. 44, if the user removes the autoinjector from his body while the injection is underway or after injection but before the end of the retarder, the spring 12 of the actuating sleeve 11 will stress said actuating sleeve 11 returning from the lower body 10. This movement of the actuating sleeve 11 will draw the control slide 9 axially downwards in FIG. 44 by cooperation between the upper shoulder 119 and the projection 92 of the slider. Therefore, the control ring 2 will again be released in rotation by the control slide 9, and the spring 3 will stress this control ring more in rotation, which will cause retraction of the syringe and of the needle inside the body. The actuating sleeve 11, on completion of movement, will be locked as described previously. Therefore, even if the user removes the autoinjector before full distribution of the product, the needle safety device is operative.

In normal operation, the injection is terminated and as is described hereinbelow the piston rod 5 will release the rotation of a trigger 19, optionally with some delay if a retarding device is used. From the moment when the trigger 19 has performed predefined rotation, a projection 191 of the trigger 19 will cooperate with the upper shoulder 95 of the control slide 9, and this control slide 9 will be moved axially downwards in FIG. 44, which will release rotation of the control ring 2, as described previously.

Figure 45:
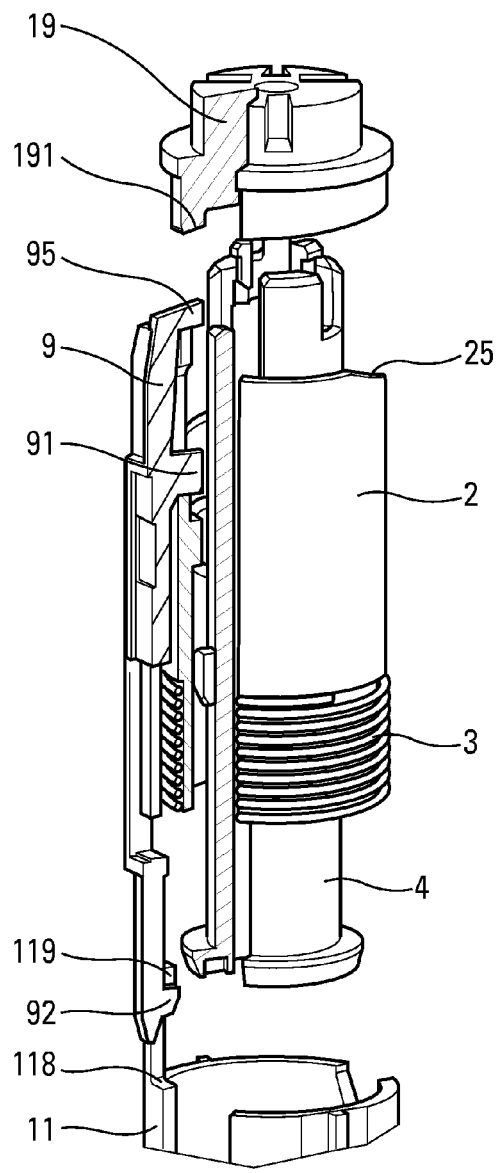
FIGS. 45 and 46 are view similar to FIGS. 43 and 44, on completion of injection.
Figure 46:
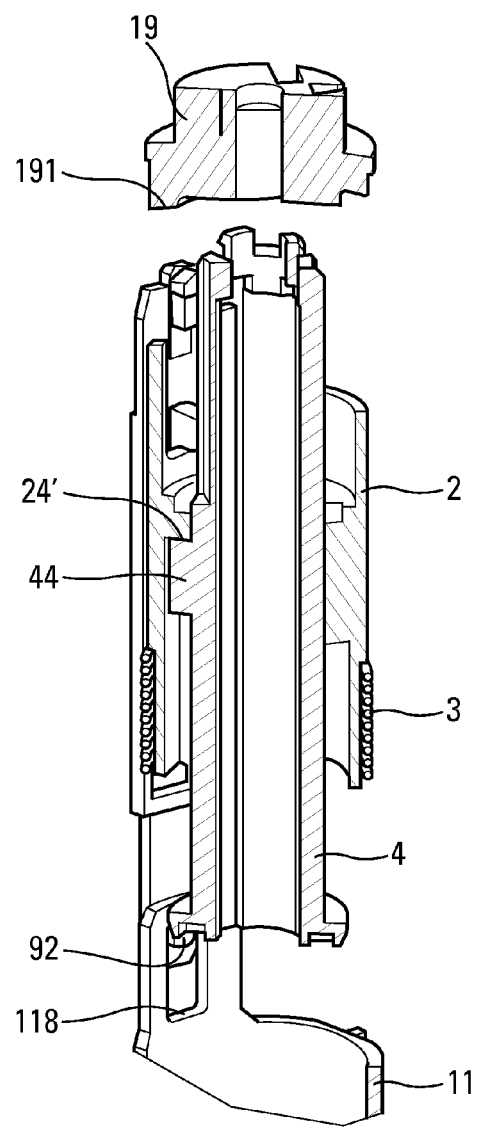

FIGS. 45 and 46 illustrate retraction of the needle with rotation of the ring 2 that will bring the projection 44 of the control sleeve opposite an internal groove of the ring 2, which will cause, under the effect of the spring, axial return deformation of the control sleeve 4 inside the control ring 2 and therefore retraction of the syringe and of the needle.

FIGS. 19 to 26 schematically illustrate an advantageous injection lock. The autoinjector comprises injection means, comprising especially the piston rod 5, the injection spring 8 and the blocking ring 23, these injection means being blocked in a loaded position by said injection lock. The unblocking of said injection lock then causes actuation of said injection means and therefore injection of the fluid product through the needle.

Figure 19:
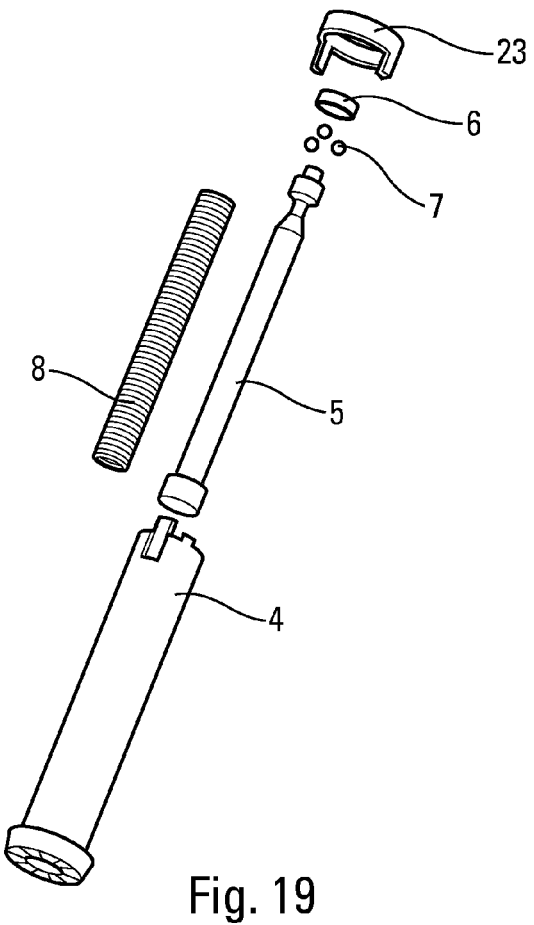
FIG. 19 is an exploded schematic view in perspective illustrating an advantageous injection lock.

As shown in FIG. 19, said injection lock comprises a control sleeve 4 arranged in said central body 1, said control sleeve 4 containing said piston rod 5 and said injection spring 8, said piston rod 5 comprising a radial recess 50 receiving at least one blockage element 7 mobile between a blocking position and an unblocking position. Said at least one blockage element 7 is preferably substantially spherical in shape. In the variant shown, there are three blockage elements 7 in the form of balls, but a different number of blockage elements and forms slightly different to these blockage elements are possible. The following description will be made however in reference to three balls, without this being limiting. Said balls 7 are stressed radially towards the exterior by said piston rod 5 and are held in the blocking position by a blockage member, which in this embodiment is formed by a blocking ring 23. This blocking ring 23 is moveable axially relative to said piston rod 5 between a locking position, in which if keeps the blockage elements 1007 in the blocking position, and an unlocking position, in which said blockage elements 1007 are released to unblock said injection lock, allowing said injection spring to move said piston rod 5 towards its injection position.

Figure 20:
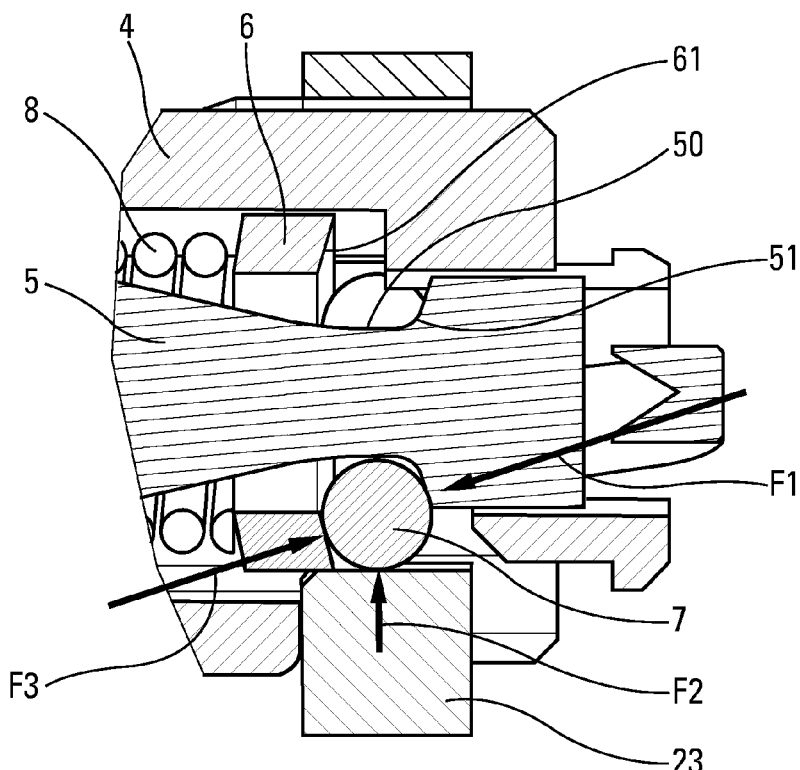
FIG. 20 is a sectional transversal schematic view of the injection lock of FIG. 19, in the blocking position.

FIG. 20 shows the injection lock in the blocking position. The injection spring 8 cooperates on the one hand with the piston rod 5 and on the other hand with a pellet support 6. This pellet support 6 is formed by a ring arranged around said piston rod 5. The piston rod 5 comprises a peripheral recess 50, provided advantageously with an inclined surface 51, formed by narrowing of the diameter of said piston rod 5. This piston rod 5 is arranged inside the control body 4 and is likely to be moved axially towards the left in FIG. 20 to push the piston of the syringe A inside the syringe and distribute the fluid product contained in said syringe through the needle.

As evident in FIG. 20, the balls 7 are arranged in said recess 50 formed in the piston rod 5 and cooperate therefore on the one hand with the inclined wall 51 of the piston rod 5 and on the other hand with the upper surface 61 of said pellet support 6.

The inclined surface 51 of the piston rod is in contact with the balls 7 such that under the effect of the compressed spring 8, said inclined surface 51 exerts a reaction force F1 on the balls 7, this force F1 not being exactly axial but directed slightly towards the exterior, stressing the balls 7 radially towards the exterior of the blocking position of FIG. 20.

The blocking ring 23 is provided radially outside the balls 7 to radially block said balls in the blocking position. In reference more particularly to FIG. 22, it is evident that the balls can be arranged in housings of the control sleeve 4, the blocking ring 23 comprising projections 231, one for each ball 7, which are positioned in contact with the balls 7 to prevent the latter from being moved radially towards the exterior.

The pellet 6 transmits the force F3 of the spring 8 to the balls 7, and the blocking ring 23 exerts a reaction force F2 on the balls 7 to prevent radial movement thereof. Therefore, it is the balls 7 which support all the forces exerted on the lock in the blocking position, with balance at three points under the effect of forces F1, F2 and F3. Such a lock is particularly stable and robust and especially resists drops tests. These tests simulate the fact of dropping the autoinjector to the floor after the cap 14 has been removed, the aim being to avoid triggering of the injection lock during this fall. In particular, no force is exerted on the structural pieces of the autoinjector, such as the central body 1 or the lower body 10. This lock accordingly avoids the risk of untimely disassembly of the device during transport or handling.

It is evident that the balls 7 could be replaced by non-spherical elements but of rounded more complex shape, for example in the form of a cylinder or bean, to further improve the stability of the lock. In this case, these non-spherical mobile elements could be made of metal, for example by steel wire cutting.

Figure 21:
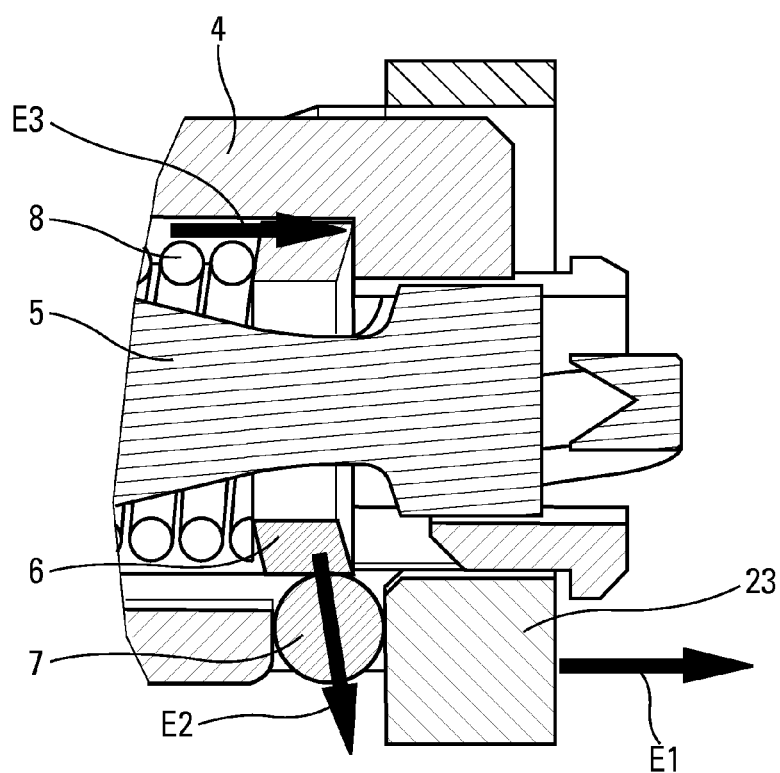
FIG. 21 is a view similar to that of FIG. 20, in the unblocking position.
Figure 22:
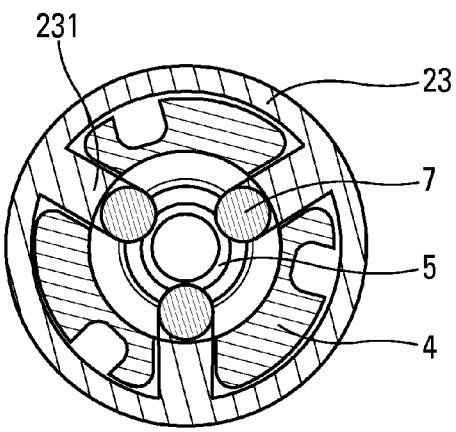
FIG. 22 is a schematic plan view in horizontal section of the injection lock of FIG. 19, in the blocking position.
Figure 23:
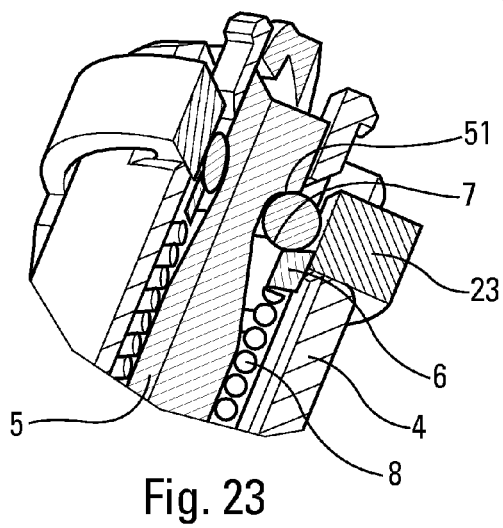
FIG. 23 is a partially cut schematic view in perspective of the injection lock of FIG. 19, in the blocking position.
Figure 24:
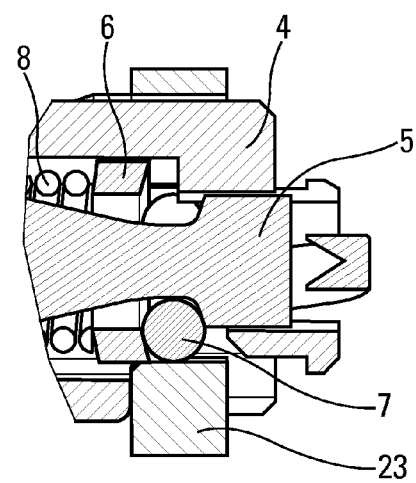
FIG. 24 is a transversal sectional schematic view of the injection lock of FIG. 19, in the blocking position.
Figure 25:
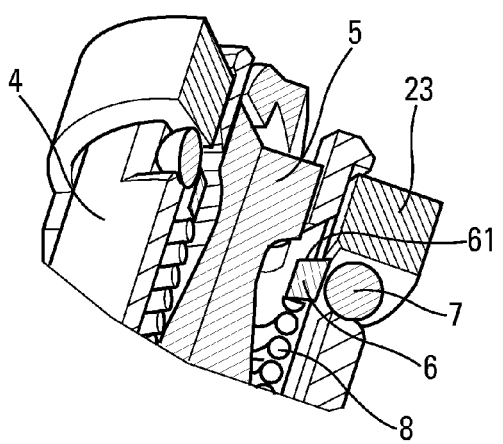
FIG. 25 is a view similar to that of FIG. 23, in the unblocking position.
Figure 26:
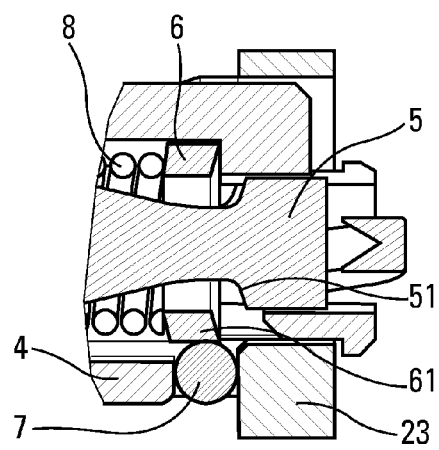
FIG. 26 is a view similar to that of FIG. 24 in the unblocking position.

When the needle of the syringe has fully penetrated the body of the user, and only after this total insertion, as is described below, the blocking ring 23 is moved according to arrow E1 in FIG. 21. The effect of this is to release the balls 7 from their blocking position, the latter being moved radially towards the exterior according to arrow E2. As a variant, the blocking ring 23 could also be moved in rotation towards a position where it releases the balls. The pellet support 6 then stops against an internal edge of the control sleeve 4, as shown by arrow E3 in FIG. 21. In this position, the piston rod 5 is no longer held by the balls 7 and it is therefore moved axially, that is, towards the left in FIG. 21, to perform injection of the product. The balls 7 can no longer return to the blocking position, prevented by the pellet 6, as is evident in FIG. 21.

With slightly different views FIGS. 23 to 26 illustrate the two positions of blocking and unblocking of the injection lock, as described above in reference to FIGS. 20 and 21.

The injection lock shown in FIGS. 19 to 26 unlocks a substantial force exerted by a compressed spring, in this case the injection spring 8, by exerting a relatively weak and easily controlled force on the blocking ring 23. In particular, the force necessary to move said blocking ring 23 into the unblocking position can represent only 10%, or even only 5%, of the force exerted by the injection spring 8. This represents a very large yield which ensures easy and reliable actuation of the device.

When the injection is finished, that is, when the piston rod 5 has reached its end position in which the piston of the syringe A has been moved to inject the fluid product, a trigger 19 is actuated to retract the syringe and therefore the needle.

During the injection phase, a locking finger 20 extends through the trigger 19 and into the central channel 151 of the upper body 15. A retardant spring 18, here a spiral spring, stresses said trigger 19 in rotation. This rotation is blocked by the locking finger 20, advantageously oblong in shape, which is adapted to turn together with said trigger 19, but that is blocked in rotation by said central channel 151 of the upper body 15. During the injection phase, the piston rod 5 moves axially, that is, towards the left in FIG. 28. As it moves, it will pull on the wire 21 that will therefore extend out of the channel 151. As the locking finger 20 is arranged inside the central channel 151, rotation of the trigger 19 is blocked. When the piston rod 5 approaches the end of the injection path, the wire 21 is completely taut and held between the piston rod 5 and the locking finger 20, and any extra movement of the piston rod 5 will therefore axially move the locking finger 20 out of said central channel 151. When the piston rod 5 reaches the end position of the end of injection, the locking finger stops cooperating with the central channel 151, and the trigger 19 and the locking finger can turn under the effect of the retardant spring 18. As evident in FIG. 31, the trigger 19 comprises an external inclined ramp 190 that can comprise a projection 191 to one side. When the trigger 19 will have described a predefined rotation, typically about one turn, this projection 191 will cooperate with the control slide 9, which will move the latter axially and trigger retraction of the needle, as has been described previously.

FIGS. 27 to 31 illustrate an advantageous retarding device.

The main aim of this retarding device, which is optional in an autoinjector, is to offset retraction of the syringe A in time and therefore of the needle out of the body of the user after completion of injection of the fluid product inside said body. This especially enables diffusion for a few seconds of the product after its injection. Such a retarder also produces a benefit for the user who no longer has to count, for example up to 10, after injection, the time taken for this counting varying widely from one user to another. A retarder makes the sequence of use of an autoinjector easy.

The mechanical retarder shown in FIGS. 27 to 31 offsets this retraction by a few seconds, this delay being predeterminable.

Figure 27:
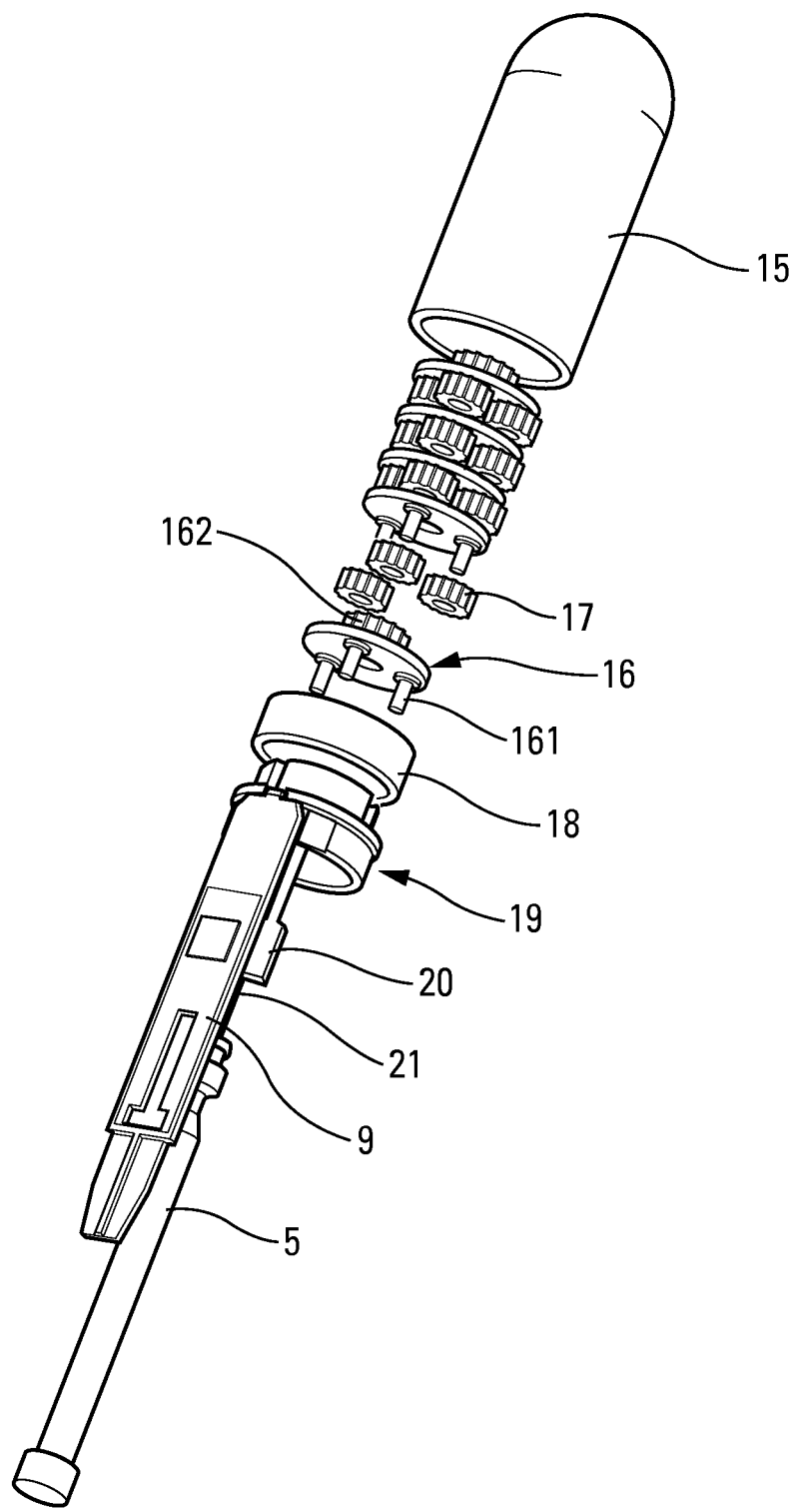
FIG. 27 is an exploded schematic view in perspective of an advantageous retarding device.

FIG. 27 illustrates an exploded schematic view of this retarding device. This comprises the upper body 15, several planetaries 16 with several satellites 17, the retardant spring 18, the trigger 19, the locking finger 20, the wire 21 and the piston rod 5. It is this piston rod 5 that will perform actuation of the retarding device when it arrives at the end of the injection path with all the product that has been injected.

Figure 28:
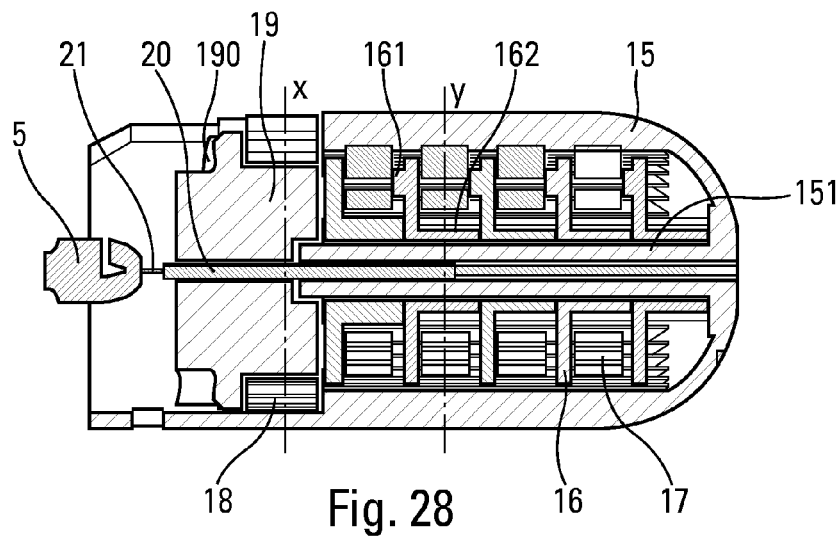
FIG. 28 is a transversal sectional schematic view of the retarding device of FIG. 27 before its actuation.
Figure 29:
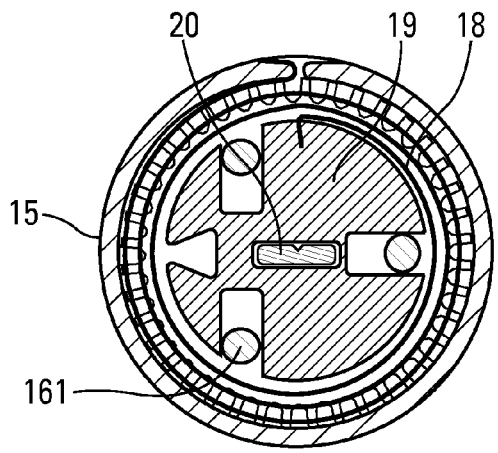
FIG. 29 is a sectional schematic view according to the cutting line X of FIG. 28.
Figure 30:
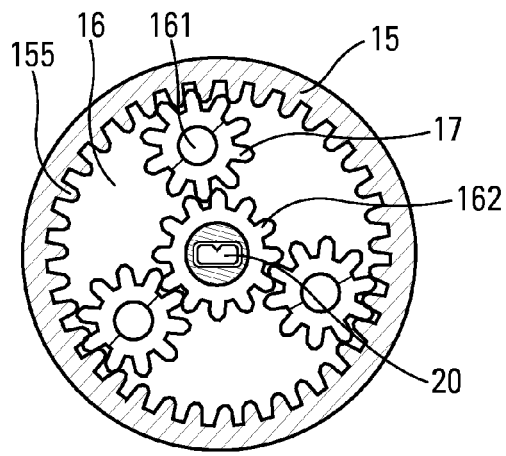
FIG. 30 is a sectional schematic view according to the cutting line Y of FIG. 28.
Figure 31:
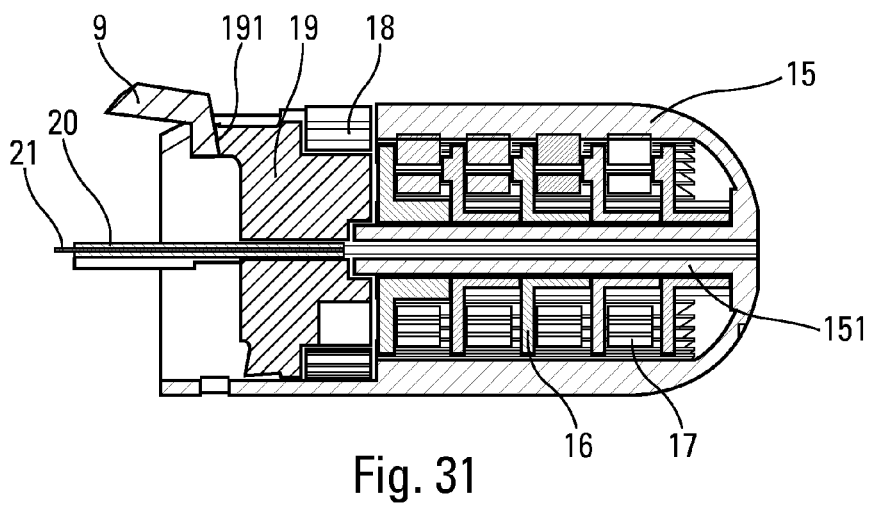
FIG. 31 is a view similar to that of FIG. 28, at the end of actuation of the retarding device.
Figure 32:
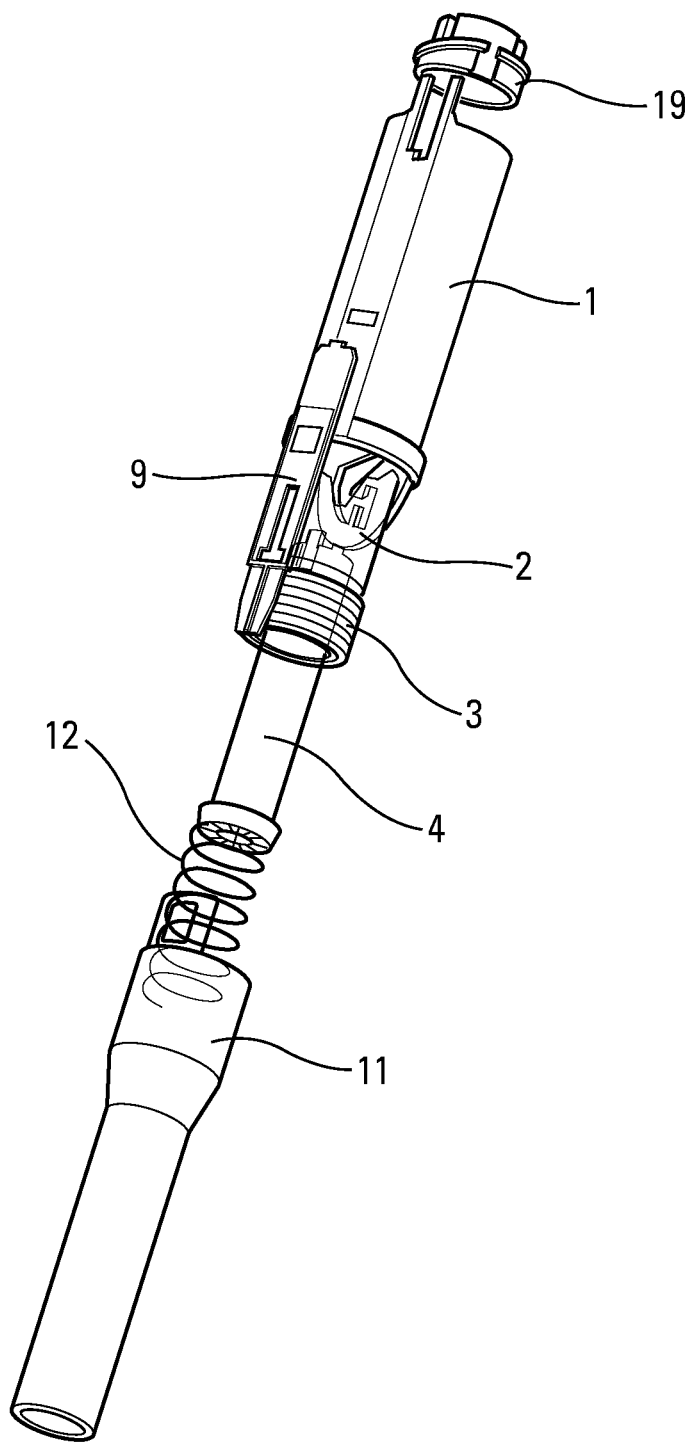
FIG. 32 is an exploded schematic view in perspective of an advantageous syringe movement mechanism.

FIG. 28 shows the retarding device before its actuation. It is evident that the actuation rod 5 is connected to the locking finger 20 by means of the wire 21. In this position, the wire 21 and the locking finger 20 extend inside a central channel 151 of the upper body 15 and into the trigger 19. The upper body 15 comprises a gear 155 on its lateral internal surface, as clearly evident in FIG. 30. This internal gear 155 of the upper body 15 cooperates with a plurality of satellites 17 that are assembled on planetaries 16. In the example shown in FIG. 28, there are several planetaries stacked axially on each other. The planetaries 16 comprise a plate in the form of a disk on which are formed to one side satellite support rods 161 which each rotatably receive a satellite 17. In the example shown, there are three satellites 17 to each stage such that there are three rods 161. Each planetary 16 associated with its satellites 17 forms one stage of the retarding device. On the other side of the plate in the form of a disk the planetary 16 comprises a gear 162 adapted to cooperate with the satellites 17 of the adjacent stage. Therefore, as is evident in FIG. 30, the retarding device utilizes the principle of epicycloidal trains. Each stage of this device demultiplies and/or slows down the rotations of the previous stage.

When a retarding device is used, the trigger 19 cooperates with a first planetary 16, whereof the rods 161 extend inside said trigger 19. The gear 162 of this first planetary 16 cooperates with the satellites of a second adjacent planetary, which cooperate with the lateral gear 155 of the upper body 15, demultiplying the rotation of the first planetary and therefore of the trigger, and therefore braking this rotation. Each additional stage of the epicycloidal train forming the retarder will further demultiply these rotations, and therefore further brake the rotation of the trigger 19. Therefore, with four stages as shown in the figures, the rotation of the trigger 19 can be made as a single turn, whereas the last planetary 16 arranged at the very bottom of the upper body 15 will describe around fifty turns simultaneously.

According to the number of stages and/or according to the number of satellites and/or according to the form of the planetaries and/or according to the dimensions of the gears in play, the delay between the moment when the retarding device is triggered and the moment when the trigger 19 will have performed its predefined rotation to trigger retraction of the syringe can be adjusted fairly precisely, as is explained later. Friction braking can also be provided, for example between the satellites 17 and the internal gear 155 of the upper body 15.

The retarding device therefore offsets the moment when said trigger will actuate retraction of the needle by a predetermined time, from the moment when the injection phase is finished.

It is evident that the deployable wire principle connected on the one hand to the piston rod 5 and on the other hand to the locking finger 20 can be used without the train epicycloidal system such as shown in FIGS. 27 to 31, as will be especially described hereinbelow in reference to the second embodiment. This wire, of minimal bulk, ensures that retraction of the needle commences only once the injection phase is fully finished, especially compensating any manufacturing tolerances. More generally, the use of a wire reduces the bulk of the device. Because of this, it can be used advantageously for various functions in an autoinjector, as there is a need to pull one piece relative to another.

According to an advantageous aspect, the external shell 22 comprises several indicators which inform the user of the advance of sequences for pricking, injection and retraction. In case of use of a retarding device, display of said delay can also be provided.

Therefore, as evident in FIGS. 2a to 2f, the external shell 22 can comprise several display windows, in this case three windows 221, 222, 223, which display mobile elements during different phases of actuation, these elements comprising indicators, typically colors.

Therefore, the control slide 9, which at rest is in a first position relative to the central body 1, moves axially towards a second position during movement of the actuating sleeve 11. It remains in this second position throughout the injection phase, and returns in the direction of its first position during retraction of the needle. It is only when the actuating sleeve returns to its second projected position that the control slide reaches this first position. This control slide 9 can comprise one or more color indicators, for example a red zone as evident in FIG. 1. This slider can therefore be used to indicate on the one hand the projected position of the actuating sleeve 11 (first position) and on the other hand the pricking and injection phase (second position).

The trigger 19, which triggers the retraction of the needle on completion of injection, can also comprise an indicator, for example a red zone which displays when said trigger has performed its predefined rotation and actuated retraction of the needle.

Therefore, the first display window 221 can be the window for completion of injection, that is, when a predefined color, red for example, appears in the window 221, the injection is finished and the syringe has been retracted. The user therefore knows that when this first display window is red he can remove the autoinjector from his body in complete safety. This indication can be supplied for example by the trigger 19.

The second display window 222 can be that of the phases of pricking and injection, which changes to red at the start of the pricking phase at the end of the injection phase. This prevents the user from removing the autoinjector from his body during these phases, which can last several seconds. This indication can be supplied by the actuator slider 9.

The third display window 223 can be that of the actuating sleeve 11, with the red displayed when the actuating sleeve 11 is in a projected position out of the lower body. This third display window 223 is therefore red prior to actuation, then again after use when the actuating sleeve 11 is locked in the safety position. This indication can be supplied by the control slide 9. In the example shown, the red zone of the actuator slider 9 moves from the third display window 223, prior to actuation (FIG. 2a), to the second display window 222 (FIG. 2c) when the actuating sleeve is in the actuation position where it triggers the pricking phase. During this transition, said red zone is not evident as it is located between said windows 223 and 222 (FIG. 2b). During the phases of pricking and injection, the control slide stays in its second position (FIG. 2c & FIG. 2d). When the control slide 9 is again moved axially towards its first position by the trigger 19, to actuate retraction of the needle, the red zone changes back from the second window 222 to the third window 223, being invisible again (FIG. 2e), to finally reappear in the third window 223 when the actuating sleeve is locked in the second projected position (FIG. 2f).

In this configuration, the combination of red in the first and third display windows 221 and 223 ensures the end of the process of use of the autoinjector, with the needle retracted and the actuating sleeve 11 locked, ensuring optimal safety.

Of course, other means of display or indication are also possible and said external shell 22 can comprise any number of display windows, of any form and dimension, and that could be positioned differently to the variant shown in the figures. The same window can especially display several different functions.

Optionally, in the first display window 221 or in another display window, for example an additional display window, the state of the retarding device can be displayed, for example with a count. This could be done for example with numerical values inscribed on the lateral external edge of the trigger which moves progressively into an appropriate display window and which in seconds displays the count of the retarder. Other variants are of course also possible.

This external shell 22 can also comprise a button or buttons for pricking and/or retraction of the needle if the autoinjector provides such buttons to perform pricking and/or retraction of the needle.

The external shell 22 could also comprise a temperature indicator of the product to be injected. In fact, many products to be injected are stored at 8° and it is often recommended to bring them out 30-60 minutes in advance. If the product is too cold at the moment of the injection, this can cause pain for the patient. For example, the shell 22 could comprise temperature display of the tank containing the product to be injected. As a variant, a label could also be provided which changes color with temperature. This temperature indicator could be provided on the shell, or on the tank, especially the syringe, and be visible through a window of the shell.

FIGS. 47 to 74c illustrate several variants of a second embodiment of the invention. This second embodiment relates to a simplified autoinjector, comprising fewer pieces, and therefore simpler and less costly to make and assemble.

In the variant of FIG. 47 of this second embodiment, the autoinjector comprises a lower body 1010, an actuating sleeve 1011, a spring 1012 of the actuating sleeve, a cap 1014, a control sleeve 1004, a piston rod 1005, a pellet support 1006, three blockage elements 1007, here in the form of balls, an injection spring 1008, a click member 1500, a wire 1021, and an external shell 1022.

The cap 1014 especially locks the autoinjector during transport and storage. As this cap is installed on the lower body 1010, it prevents any actuation of the actuating sleeve 1011 and therefore any triggering of the autoinjector.

As for the first embodiment, the syringe A is a pre-filled syringe. It comprises advantageously a needle cap B which protects and isolates the needle prior to use of the autoinjector. Advantageously, this needle cap B is removed automatically at the moment when the cap 1014 is removed from the lower body 1010.

It is evident that this second embodiment has several elements similar to the first embodiment, these similar elements being designated by reference numerals similar to those of the first embodiment, augmented by 1000. Therefore, for example, the actuating sleeve reference 11 in the first embodiment is now reference 1011. Consequently, in the description of this second embodiment, it is mainly the differences relative to the first embodiment that is described, given that the other elements and functions remain similar, if not identical, between the two embodiments.

The principal difference in this second embodiment is that the tank, in this case the syringe A, is fixed relative to the lower body 1010, relative to the control sleeve 1004 and relative to the external shell 1022. Therefore, to perform pricking of the needle only the actuating sleeve slides relative to the rest of the autoinjector. In this second embodiment there is therefore no device for syringe movement.

FIGS. 48a to 48e illustrate the sequences of the use of the autoinjector of FIG. 47.

In FIG. 48a, the autoinjector is in a rest position prior to use, the cap 1014 having been removed.

When the user wants to use the autoinjector, he takes the device, for example at the level of the external shell 1022 and presses the actuating sleeve 1011, which in a first projected position projects out of the lower body 1010, against the part of the body where he wants to perform the injection. In FIG. 48b, it is evident that the pressure exerted by the user on the actuating sleeve 1011 causes sliding thereof towards the interior of the lower body 1010, which reveals the needle and therefore its pricking due to the pressure exerted by the user on the autoinjector.

When the actuating sleeve 1011 reaches its actuation position, which is its end position inside the lower body 1010, it causes triggering of the injection phase that is shown in FIGS. 48c and 48d. It is noted that the piston rod 1005 slides inside the syringe A by pushing the piston thereof under the effect of the injection spring 1008. The product is therefore distributed.

On completion of the injection, when the user removes the autoinjector from the injection site, the actuating sleeve 1011 is again shifted out of the lower body 1010 towards a second projected position, under the effect of the spring of the actuating sleeve, with locking of said actuating sleeve 1011, which ensures absolute safety for the user and avoids any risk of injury with the needle after use of the device. It is evident that the first and second projected positions of the actuating sleeve, which, in the example shown, are different positions, could optionally be identical.

In this second embodiment, as evident especially in FIGS. 49a to 52, said actuating sleeve 1011 also comprises a flexible foot 1110 that is flexible laterally only, that is, it deforms in the direction peripheral of the actuating sleeve 1011 only. An actuating sleeve 1011 provided with such a flexible foot is even simpler to mold than the flexible foot with double flexibility of the first embodiment, which is favorable from the point of view of manufacturing costs. With a foot flexible laterally only, there is also a gain in radial bulk, which especially improves the aesthetics of the autoinjector. The flexible foot 1110 advantageously comprises a rod part 1111 that is flexible and which terminates in a head part 1112.

In a first variant, illustrated in FIG. 51, said flexible foot 1110 is adapted to deform laterally relative to said lower body 1010 on the one hand when said actuating sleeve 1011 is moved from its first projected position towards its actuation position and on the other hand when said actuating sleeve 1011 is moved from its return actuation position towards its second projected position. In this case, the head 1112 of the flexible foot must overcome resistance to deform laterally at the start of the actuation, to create a sort of precompression which ensures that when the actuating sleeve will slide towards the interior of the lower body 1010, the needle will suddenly penetrate the injection site as far as its planned injection position. In the example of FIG. 51, this resistance is formed by a shoulder 1019 of the lower body 1010.

Preferably however, in a second variant shown in FIGS. 50a, b, c and 52, said flexible foot 1110 is not deformed when said actuating sleeve 1011 is moved from its first projected position, prior to actuation, towards its actuation position, and said flexible foot is deformed laterally only when said actuating sleeve 1011 is moved from its actuation position towards its second projected position, at the end of use. In this variant, prior to actuation, the actuating sleeve 1011 is connected to said lower body 1010 by at least one scored bridge 1500. This embodiment especially allows easy molding, and therefore reduced manufacturing costs, adaptation and management of the breaking force of the scored bridges facilitated by the dimensioning of these bridges, and an evidence of use function.

FIG. 52 illustrates two scored bridges 1500, adapted to break and therefore enable sliding of the actuating sleeve 1011 relative to the lower body 1010 when the user presses the autoinjector on the injection site using predetermined pressure.

When the actuating sleeve 1011 returns from its second actuation position towards its projected position, under the effect of the spring 1012, when the user removes the autoinjector from the injection site, the operation of the flexible foot 1110 can be identical to that described within the scope of the first embodiment, with an inclined groove, a final reception zone and an axial shoulder cooperating with the head of the flexible foot to block it in the second projected position.

In a variant, the lower body 1010 can comprise a shoulder 1019 that extends axially towards the interior by a ramp 1018, for example formed by a groove, which is at least partially inclined. Therefore, when the actuating sleeve 1011 returns from its actuation position towards its second projected position the head 1112 of the flexible foot 1110 will be deformed laterally by said ramp 1018, to finally returns to clip in under the projection 1019 in the second projected position to block the actuating sleeve.

In the variant of FIG. 51, this same projection 1019 can cooperate with the head 1112 of the flexible foot 1110 at the same time at the start of actuation to create precompression and at the end of actuation to block the actuating sleeve in the second projected position. Of course, two different shoulders can also be provided to carry out these two functions.

It is evident that the flexible foot 1110 can be fixed to said actuating sleeve 1011 only at the level of its rod part 1111, with in this case the head 1112 forming a free end of said flexible foot. By way of variant, the flexible foot could also be fixed to said actuating sleeve on two sides, with the head 1112 arranged between the two fastening points. This execution reinforces especially the robustness of the flexible foot. This variant could also be adapted to the flexible foot of the first embodiment.

In the variants of FIGS. 49a to 52, the flexible foot 1110 of the actuating sleeve 1011 cooperates advantageously with an opening 103, an inclined groove 104, a final reception zone 105 and an axial shoulder 106 of the body 1010 that are similar to these same elements described previously in reference to FIGS. 4 to 18.

FIGS. 72 to 74c illustrate another variant embodiment of the actuating sleeve. In this variant, the reference numerals will be similar to those above, but augmented by 1000. Therefore for example, the actuating sleeve will be referenced 2011. In this particular variant, the functions of the actuating sleeve 2011 and of the body 2010 are reversed, the body 2010 comprising the flexible foot 2110, and the actuating sleeve 2011 comprising the profile that will cooperate with said flexible foot 2110. The operation however remains similar to that described previously, with the flexible foot 2110 that will progressively slide in said profile, and especially in an inclined groove 2104 that connects an opening 2103 to a final reception zone 2105. To lock the device at the end of actuation in the final reception zone 2105, the flexible foot 2110 will clip onto the shoulder 2106, as is evident in FIG. 74c. As described previously, the flexible foot must advantageously overcome resistance to deform at the start of the actuation to create a sort of precompression which ensures that when the actuating sleeve 2011 will slide towards the interior of the lower body 2010 the needle will suddenly penetrate the injection site as far as its planned injection position. In the example of FIGS. 72 to 74C, this resistance is formed by a shoulder 2019 of the actuating sleeve 2011. It is evident that the flexible foot 2110 can be formed monobloc on the body 2010, or as a variant be formed on a separate piece assembled on said body 2010, for example for reasons of simplicity and/or molding.

FIGS. 53a, b, 54a, b, 57a, b, c and 58a, b, c illustrate adaptation to the second embodiment of the injection lock described in the first embodiment.

As described previously, the autoinjector comprises injection means, comprising especially the piston rod 1005 and the injection spring 1008, these injection means being blocked in a loaded position by said injection lock. The unblocking of said injection lock causes actuation of said injection means and therefore injection of the fluid product through the needle.

As shown in the different FIGS. 53, 54, 57 and 58 said injection lock comprises a control sleeve 1004 arranged in said external shell 1022, said control sleeve 1004 containing said piston rod 1005, said injection spring 1008 and a pellet support 1006. In the blocking position shown in the different FIGS. 53 and 57, the injection spring 1008 cooperates on the one hand with the piston rod 1005 and on the other hand with said pellet support 1006. This pellet support 1006 is formed by a ring arranged around said piston rod 1005. Said piston rod 1005 comprises at least one radial recess 1050 receiving at least one blockage element 1007 mobile between a blocking position and an unblocking position. Advantageously, there are three blockage elements 1007, preferably substantially spherical in shape, especially in the form of balls, but a different number of blockage elements and rounded forms different to these blockage elements are possible. Said blockage elements 1007 are stressed radially towards the exterior by said piston rod 1005 and are held in the blocking position by a blockage member, which in this second embodiment is formed by said control sleeve 1004. This control sleeve 1004 is moveable axially relative to said piston rod 1005 between a locking position in which it holds the blockage elements 1007 in the blocking position, and an unlocking position in which said blockage elements 1007 are released to unblock said injection lock, allowing said injection spring to move said piston rod 1005 towards its injection position.

As evident more particularly in FIGS. 57*a* and 58*a*, the control sleeve 1004 comprises one or more windows 1400 that allow the blockage elements 1007 to move when the control sleeve has been moved towards its unlocking position, shown especially in FIG. 58. The movement of the control sleeve 1004 from its locking position towards its unlocking position is performed by a projection 1411 of the actuating sleeve 1011, which will cooperate with a shoulder 1410 of the control sleeve 1004 such that the control sleeve 1004 is in the unlocking position when the actuating sleeve 1011 is in the actuation position. Since said piston rod 1005 is now not blocked by said blockage elements 1007, it is moved out of the control sleeve by said precompressed injection spring 1008 to move the piston into the tank and inject product through the needle. This type of lock enables unblocking with little effort, ensuring sound and tactile comfort for the user during injection.

Advantageously, the autoinjector comprises a sound and/or tactile indication device 1500 to indicate by an audible or by a tactile indication to the user that the injection phase is finished. This device is described hereinbelow in relation to three variants of the second embodiment, but it could also be adapted to an autoinjector made according to the first embodiment.

According to a first variant embodiment, this sound and/or tactile indication device 1500 comprises a central piece 1501 provided with at least one lateral piece 1502 connected to said central piece 1501 by a pliable and/or scored link 1503. In the example shown in FIGS. 55 to 59*c*, there are two lateral pieces 1502, each connected to the central piece by a scored link.

The central piece 1501 is connected to said piston rod 1005 by said wire 1021, which is fixed on the one hand to said central piece 1501 and on the other hand to said piston rod 1005. In the blocking position of the injection lock, before the start of the injection, the wire 1021 is wound around the piston rod and the central piece 1501 is arranged outside the control sleeve 1004. When the control sleeve 1004 is moved towards its unlocking position, shown especially in FIG. 58*a*, an upper edge of said control sleeve 1004 makes contact with said lateral pieces 1502. During the injection, when the piston rod 1005 moves relative to the control sleeve 1004, the wire 1021 will progressively unwind until it is stretched on completion of injection, as shown in FIG. 58*b*. From this moment, the wire 1021 will exert traction on the central piece 1501, under the effect of the reaction of the upper edge of the control sleeve 1004 causing movement and/or deformation of the lateral pieces.

In the example shown with scored links 1503, the latter break, allowing the lateral pieces 1502 to move above the central piece 1501, and therefore the control sleeve 1004 to move axially relative to the external shell 1022, as evident especially in FIG. 59*a*. As this movement happens under the pressure exerted by the injection spring 1008 on the control sleeve 1004, it is relatively brusque and creates a shock between the control sleeve 1004, the lateral pieces 1502 and/or the external shell 1022. This shock is audible and/or tactile for the user who therefore receives information on the completion of injection. After actuation of this sound and/or tactile indication device, the wire 1021 is no longer fully stretched, as illustrated schematically in FIGS. 59*a* and 59*b*.

FIGS. 60 to 64*c* illustrate a second variant of the sound and/or tactile indication device. In this second variant, the central piece is omitted. The sound and/or tactile indication device 1500 comprises a mobile element that is here formed by the control sleeve 1004, which comprises at its distal end relative to the needle one or more deformable feet 1510, which on completion of injection will stop against the external shell 1022. This control sleeve 1004 is in a first position relative to the external shell 1022 prior to actuation of the autoinjector, as shown in FIG. 64*a*. During actuation, the opening of the injection lock, and therefore the start of the injection phase, causes movement of the control sleeve 1004 towards a second position, evident in FIG. 64B. Here a central piece called a key 1120 advantageously replaces the wire of the preceding first variant. This key 1120, especially evident in FIGS. 63*a* and 63*b*, comprises a rod part 1121 that extends inside the piston rod 1005, this rod part being similar to the wire of the first variant. The key 1120 also comprises a head part 1122, arranged at the upper end (or distal end relative to the needle) of said key. This head part cooperates with said deformable feet 1510 of the control sleeve 1004 to prevent it from deforming radially towards the interior. Because of this, these deformable feet 1510 block said control sleeve in its second position relative to said external shell 1022. The lower end (or proximal end relative to the needle) of the rod part 1121 cooperates with the piston rod 1005 on completion of injection, causing sliding of said key 1120 relative to the control sleeve 1004 and to the external shell 1022. Therefore, after this sliding, the head part 1122 no longer cooperates with the feet 1510 of the control sleeve, which can deform radially towards the interior. The effect of this is to unblock the control sleeve 1004 that is then shifted towards a third position against said external shell 1022 under the effect of the force exerted by the injection spring 1008. This creates an audible shock or otherwise detectable by the user who now knows that the injection is finished.

Advantageously, the external shell 1022 comprises one or more, especially three, display windows 1023 in which said deformable feet 1510 become visible at the same time as they tap against the external shell. This allows visual indication simultaneously to the sound and/or tactile indication.

Advantageously, said at least one display window 1023 is formed on or in the distal end edge of said external shell 1022, being visible at the same time in the axial direction and in the radial direction of said shell. This execution avoids masking the display window or the windows 1023 when the autoinjector is handled by the user, ensuring proper display of information displayed in said at least one display window 1023 throughout the phase of use, from start to finish. With several display windows 1023, especially three, distributed around the distal end edge of the body 1022, this ensures perfect display irrespective of the orientation of the autoinjector at the moment of its use.

The variant embodiments of the second embodiment of the autoinjector described above therefore define a control sleeve 1004 having three different positions: prior to injection when it is in the locking position, during injection when it is in the unlocking position, and after injection when it has actuated the sound and/or tactile indication device. This easily displays these three distinct positions in a suitable display window 1221. Of course, the external shell 1022 of this second embodiment could also comprise several display windows, as described in the first embodiment.

FIGS. 65 to 71 illustrate a third variant embodiment of the sound and/or tactile indication device. In this variant, which is similar to the second variant above, the mobile element of the sound and/or tactile indication device is not formed by the control sleeve 1004 but by the support pellet 1006 on which the injection spring 1008 is supported. FIGS. 66a and 66b shows this support pellet, which comprises one or more deformable feet 1520, which are similar to the deformable feet 1510 of the control sleeve 1004 of the second variant above. The operation is also similar, with the key 1120 which blocks by its head 1122 the radial deformation of said feet 1520, which blocks the pellet support relative to the external shell. When the piston rod has the key 1120 slide on completion of injection, by traction on the rod part 1121, the head part 1122 of the key 1120 will release said feet 1520, which deform radially towards the interior and will allow said pellet support 1006 to be projected against said external shell, creating a sound and/or tactile indication. Advantageously, as described previously, a visual indication is also supplied by a display window or windows 1023 of the external shell that show the deformable feet 1520 of the pellet support 1006.

FIGS. 69 to 71 illustrate in more detail the operation of the sound and/or tactile indication device. In FIG. 69, the deformable foot 1520 is prevented from deforming radially towards the interior by the presence of the head part 1122 of the key 1120. In FIG. 70, the key has been moved by the piston rod and consequently the deformable foot 1520 has deformed radially towards the interior. This has caused movement of the support pellet 1006 in the external shell, with a shoulder 1521 of the deformable foot which stops on a part of said external shell, generating the sound and/or tactile indication, for example an audible or sensitive vibration. Simultaneously, the end of the deformable foot 1520 has been positioned in the window 1023 of the external shell 1022, as is evident in FIG. 70. FIG. 71 illustrates the end of the injection, with the piston rod 1005 that will pull on the rod part 1121 of the key 1120 to move the latter.

The present invention applies to devices used especially for treatment of auto-immune diseases, for example of rheumatoid arthritis, multiple sclerosis, Crohn's disease type, for treatments against cancer, for antiviral treatment, for example of hepatitis type, for treatment against diabetes, for treatments against anemia or for treatment of stress, for example in the event of anaphylactic shock.

Even though the present invention has been described in reference to several advantageous modes and variant embodiments, which combine several functional modules, it is understood that the different modules described can be used independently of each other. In particular, the actuating sleeve and/or the device for movement of syringe for pricking and/or retraction and/or the injection lock and/or the retarding device and/or the sound and/or tactile indication device could be used independently of each other. Pricking of the needle and/or retraction of the needle after injection could be controlled by one or more button(s). The sound and/or tactile indication device of the second embodiment could be used with an autoinjector of the type described in the first embodiment. Other modifications are also possible for the expert without departing from the scope of the present invention such as defined by the attached claims.

The invention claimed is:

1. An autoinjector comprising a lower body receiving a tank, said tank containing fluid product and comprising a piston and a needle, said autoinjector comprising:
    injection means to inject said fluid product through said needle when said needle is in an injection position; and
    a tank movement device for retracting said needle from the injection position after injection of the fluid product, a trigger, actuated by said injection means, actuating said tank movement device after injection of the fluid product so as to retract said needle, said trigger comprises a projection adapted to actuate said tank movement device after a predefined rotation of said trigger;
    said autoinjector comprising a retarding device adapted to delay during a predetermined time the actuation of said tank movement device by said trigger after injection of the fluid product, to delay retraction of said needle by said predetermined time after the end of injection;
    wherein said retarding device comprises an epicycloidal train having at least one stage wherein each stage of said epicycloidal train comprises a planetary associated with at least one satellite.

2. The autoinjector according to claim 1, in which said trigger is stressed in rotation by a retardant spring, a locking finger arranged in said central channel blocking said rotation of said trigger.

3. The autoinjector according to claim 2, in which said locking finger is removed from said central sleeve by said injection means, on completion of injection.

4. The autoinjector according to claim 2, in which said injection means comprise a piston rod connected to said locking finger by a wire.

5. The autoinjector according to claim 1, in which said projection is formed on an external inclined ramp of the trigger, said projection axially moving a control slide of the tank movement device.

6. The autoinjector according to claim 1, in which each planetary comprises, on one side, at least one rod, each rod rotatably receiving a satellite, and, on the other side, a gear co-operating with the satellites of the adjacent stage.

7. The autoinjector according to claim 1, in which said retarding device includes an upper body provided with a central sleeve and with a gear on its lateral internal surface, said gear co-operating with said satellites.

8. The autoinjector according to claim 1, in which said epicycloidal train comprises at least two planetaries, a first planetary being driven in rotation by said trigger, the satellites of said first planetary driving said second planetary in rotation, the rotation of said second planetary being demultiplied so as to brake the rotation of the trigger.

9. The autoinjector according to claim 1, wherein the piston and needle are part of a pre-primed syringe.

10. The autoinjector according to claim 1, wherein the epicycloidal train has four stages.

11. An autoinjector comprising a lower body receiving a tank, said tank containing fluid product and comprising a piston and a needle, said autoinjector comprising:
    an injector comprising a piston rod and an injection spring configured to inject said fluid product through said needle when said needle is in an injection position; and a tank movement device for retracting said needle from the injection position after injection of the fluid product, a trigger, actuated by said injector, actuating said tank movement device after injection of the fluid product so as to retract said needle, said trigger comprises a projection adapted to actuate said tank movement device after a predefined rotation of said trigger;

said autoinjector comprising a retarding device adapted to delay during a predetermined time the actuation of said tank movement device by said trigger after injection of the fluid product, to delay retraction of said needle by said predetermined time after the end of injection;

wherein said retarding device comprises an epicycloidal train having at least one stage, wherein each stage of said epicycloidal train comprises a planetary associated with at least one satellite, and advantageously three satellites.

* * * * *